US012618840B2

(12) United States Patent
Bae et al.

(10) Patent No.: US 12,618,840 B2
(45) Date of Patent: May 5, 2026

(54) ANTIBODY FOR DETECTING ACETYLATION OF COX2 PROTEIN, AND USES THEREOF

(71) Applicant: KYUNGPOOK NATIONAL UNIVERSITY INDUSTRY-ACADEMIC COOPERATION FOUNDATION, Daegu (KR)

(72) Inventors: Jae-Sung Bae, Daegu (KR); Hee Kyung Jin, Daegu (KR); Ju Youn Lee, Daegu (KR)

(73) Assignee: KYUNGPOOK NATIONAL UNIVERSITY INDUSTRY—ACADEMIC COOPERATION FOUNDATION, Daegu (KR)

( * ) Notice: Subject to any disclaimer, the term of this patent is extended or adjusted under 35 U.S.C. 154(b) by 1081 days.

(21) Appl. No.: 17/753,702

(22) PCT Filed: Sep. 18, 2020

(86) PCT No.: PCT/KR2020/012647
§ 371 (c)(1),
(2) Date: Mar. 11, 2022

(87) PCT Pub. No.: WO2021/054778
PCT Pub. Date: Mar. 25, 2021

(65) Prior Publication Data
US 2023/0125690 A1     Apr. 27, 2023

(30) Foreign Application Priority Data

Sep. 20, 2019     (KR) ........................ 10-2019-0116290

(51) Int. Cl.
| | |
|---|---|
| *G01N 33/573* | (2006.01) |
| *A61K 39/00* | (2006.01) |
| *A61P 25/28* | (2006.01) |
| *C07K 16/40* | (2006.01) |
| *C07K 16/44* | (2006.01) |
| *G01N 33/68* | (2006.01) |

(52) U.S. Cl.
CPC ............ *G01N 33/573* (2013.01); *A61P 25/28* (2018.01); *C07K 16/40* (2013.01); *C07K 16/44* (2013.01); *G01N 33/6893* (2013.01); *G01N 33/6896* (2013.01); *A61K 2039/505* (2013.01); *C07K 2317/34* (2013.01); *C07K 2317/565* (2013.01); *G01N 2333/90245* (2013.01); *G01N 2440/10* (2013.01); *G01N 2800/2821* (2013.01); *G01N 2800/7095* (2013.01)

(58) Field of Classification Search
CPC ............ G01N 33/573; G01N 2440/10; G01N 2800/2821; G01N 2800/7095; C07K 16/40; C07K 2317/34; C07K 2317/565; A61K 2039/505
See application file for complete search history.

(56) References Cited

U.S. PATENT DOCUMENTS

| | | | |
|---|---|---|---|
| 4,737,456 | A | 4/1988 | Weng et al. |
| 4,816,567 | A | 3/1989 | Cabilly et al. |
| 5,565,332 | A | 10/1996 | Hoogenboom et al. |
| 5,573,905 | A | 11/1996 | Lerner et al. |
| 2003/0220306 | A1 | 11/2003 | Simmons et al. |
| 2010/0216882 | A1 | 8/2010 | Serhan et al. |

FOREIGN PATENT DOCUMENTS

| | | |
|---|---|---|
| WO | 2016/038608 A1 | 3/2019 |
| WO | 2019/182191 A1 | 9/2019 |
| WO | 2019/235824 A1 | 12/2019 |

OTHER PUBLICATIONS

Creminon et al. Differential measurement of constitutive (COX-I) and inducible (COX-2) cyclooxygenase expression in human umbilical vein endothelial cells using specific immunometric enzyme immunoassays Biochimica et Biophysica Acta 1254 (1995) 341-348. (Year: 1995).*

Goel et al. Plasticity within the Antigen-Combining Site May Manifest as Molecular Mimicry in the Humoral Immune Response. J Immunol (2004) 173 (12): 7358-7367. (Year: 2004).*

Lloyd et al.Modelling the human immune response: performance of a 1011 human antibody repertoire against a broad panel of therapeutically relevant antigens. Protein Engineering, Design & Selection vol. 22 No. 3 pp. 159-168, 2009. (Year: 2009).*

Rabia et al Understanding and overcoming trade-offs between antibody affinity,specificity, stability and solubility (Biochemical Engineering Journal 137 (2018) 365-374) (Year: 2018).*

Lee, Ju Youn, et al., "Neuronal SphK1 acetylates COX2 and contributes to pathogenesis in a model of Alzheimer's Disease," Nature Communications, vol. 9 (2018) (15 pages).

Aïd, Saba, et al., "Targeting cyclooxygenases-1 and -2 in neuroinflammation: Therapeutic implications," Biochimie, vol. 93 (2011), pp. 46-51.

(Continued)

*Primary Examiner* — Janet L Andres
*Assistant Examiner* — Brian Hartnett
(74) *Attorney, Agent, or Firm* — Thomas I Horstemeyer, LLP

(57) ABSTRACT

The present invention relates to an antibody for detecting acetylation of COX2 protein, and uses thereof, and more specifically, to an antibody that specifically recognizes the acetylation of S565 residue of the COX2 protein; and uses thereof for diagnosing neurodegenerative diseases or inflammatory diseases. An antibody or a functional fragment thereof according to the present invention specifically binds to an acetylated residue of COX2 protein, and can thus be very effectively used for diagnosing neurodegenerative diseases, inflammatory diseases, and the like in which the degree of acetylation of S565 residue of the COX2 protein is reduced.

17 Claims, 16 Drawing Sheets

Specification includes a Sequence Listing.

(56)　　　　　　　References Cited

OTHER PUBLICATIONS

Lei, Jinping, et al., "Mechanistic Insights into a Classic Wonder Drug—Aspirin," Journal of the American Chemical Society, vol. 137 (2015), pp. 70-73.

Fernández-Alverez, A., et al., "Evaluation of epigenetic modulation of cyclooxygenase-2 as prognostic marker for hepatocellular carcinoma," Oncogenesis, vol. 1 (2012) (12 pages).

Minghetti, Luisa, "Cyclooxygenase-2 (COX-2) in Inflammatory and Degenerative Brian Diseases," Journal of Neuropathology and Experimental Neurology, vol. 63, No. 9 (2004), pp. 901-910.

Marks, James D., et al., "By-passing Immunization—Human Antibodies from V-gene Libraries Displayed on Phage," Journal of Molecular Biology, vol. 222 (1991), pp. 581-597.

Presta, Leonard G., "Selection, design, and engineering of therapeutic antibodies," J. Allergy Clin. Immunology, vol. 116, No. 4 (2005), pp. 731-736.

Johnson, Kevin S., et al., "Human antibody engineering," Structural Biology, vol. 3 (1993), pp. 564-571.

Griffiths, Andrew D., et al., "Human anti-self antibodies with high specificity from phage display libraries," The EMBO Journal, vol. 12, No. 2 (1993), pp. 725-734.

Clackson, Tim, et al., "Making antibody fragments using phage display libraries," Nature, vol. 352 (1991), pp. 624-628.

Kawamoto, Toru, et al., "Expression of Cyclooxygenase-2 In The Subserosal Layer Correlates With Postsurgiccal Prognosis of Pathological Tumor Stage 2 Carcinoma of the Gallbladder," Int. J. Cancer, vol. 98 (2002), pp. 427-434.

Aïd, Saba, et al., Targeting cyclooxygenases-1 and -2 in neuroinflammation: therapeutic implications, Biochimie., vol. 93, Issue 1 (2011), pp. 46-51.

O'Banion, M. Kerry, "Cyclooxygenase-2: Molecular Biology, Pharmacology, and Neurobiology," Critical Reviews in Neurobiology, vol. 13, Issue 1 (1999), pp. 45-82.

* cited by examiner

Human microglia

Control n=5
AD n=15

Human microglia

WT n=3
APP/PS1 n=3

FIG. 7

Light chain variable region: DNA sequence (SEQ ID NO: 37)

Signal sequence-FR1-CDR1-FR2-CDR2-FR3-CDR3-FR4

ATGAAGTTGCCTGTTAGGCTGTTGGTGCTGATGTTCTGGATTCCTGCTTCCAGATGTGATGTTTTGATGACCCAA

ACTCCACTCTCCCTGCCTGTCAGTCTTGGAGATCAAGCCTCCATCTCTTGCAGATCTAGTCAGAGCATTGTACAT

CGTAATGGATTCACCTACTTAGAATGGTACCTGCAGAAACCAGGCCAGTCTCCAAAGCTCCTGATCTACCAAGTT

TCCAACCGATTTTCTGGGGTCCCAGACAGGTTCAGTGGCAGTGGATCAGGGACAGATTTCACACTCAAGATCAGC

AGAGTGGAGGCTGAGGATCTGGGAGTTTATTACTGCTTTCAGGGTTCACATGTTCCTCCGACATTCGGTGGAGGC

ACCAAGCTGGAAATCAAA

Light chain variable region: Amino acid sequence (SEQ ID NO: 38)

Signal peptide-FR1-CDR1-FR2-CDR2-FR3-CDR3-FR4

MKLPVRLLVLMFWIPASRCDVLMTQTPLSLPVSLGDQASISCRSSQSIVHRNGFTYLEWYLQKPGQSPKLLIYQV

SNRFSGVTDRFSGSGSGTDFTLKISRVEAEDLGVYYCFQGSHVPPTFGGGTKLEIK

FIG. 8

Heavy chain variable region: DNA sequence (SEQ ID NO: 39)

Signal sequence-FR1-CDR1-FR2-CDR2-FR3-CDR3-FR4

ATGGAATGGAGCGGGGTCTTTATCTTTCTCTTGTCAGTCACTGCAGATGTCCACTCCCAGGTCCAGCTGCAGCAG

TCTGGAGCTGAGCTGGTAAGACCTGGGACTTCAGTGAAGATATCCTGCAAGGCTTCTGGCTACACCTTCACTGAC

TACTTACTAGGTTGGGTAAAGCAGAGGCCTGGACATGGACTTGAGTGGATTGGAGATATTTACCCTGGAGGTACT

TATATTAAGTACAATGAGAAGTTCAAGGGCAAGGCCACACTGACTGCAGACACATCCTCCAGCACTGCCTACATG

CAACTCAGTAGCCTGACATCTGAGGACTCTGCTGTCTACTTCTGTGCAAGAGGGAGGAACGACGAGAAGGGGGAC

TACTGGGGTCAAGGAACCTCAGTCACCGTCTCCTCA

Heavy chain variable region: Amino acid sequence (SEQ ID NO: 40)

Signal peptide-FR1-CDR1-FR2-CDR2-FR3-CDR3-FR4

MEWSGVFIFLLSVTADVHSQVQLQQSGAELVRPGTSVKISCKASGYTFTDYLLGWVKQRPGHGLEWIGDIYPGGT

YIKYNEKFKGKATLTADTSSSTAYMQLSSLTSEDSAVYFCARGRNDEKGDYWGQGTSVTVSS

FIG. 9

Light chain: DNA sequence (SEQ ID NO: 41)

Signal sequence-FR1-CDR1-FR2-CDR2-FR3-CDR3-FR4

ATGGATTCACAGGCCCAGGTTCTTATGTTACTGCTGCTATGGGTATCTGGTACCTGTGGGGACATTGTGATGTCA

CAGTCTCCATCCTCCCTAGCTGTGTCAGTTGAAGAGAAGGTTAATATGAGCTGCAAGTCCAGTCAGAGCCTTTTA

TATAGTAGAAATCAAAAGAACTACTTGGCCTGGTACCAGCAGAAACCAGGGCAGTCTCCTAAACTACTGATTTAC

TGGGCATCCACTAGGGAATCTGGGGTCCCTGATCGCTTCACAGGCAGTGGAGCTGGGACAGATTTCACTCTCACC

ATCAGCAGTGTGAAGGCTGAAGACCTGGCAGTTTATTACTGTCAGCAATATTATACCTATCCATTCACGTTCGGC

TCGGGGACAAAGTTGGAAATAAAA

Light chain: Amino acid sequence (SEQ ID NO: 42)

Signal peptide-FR1-CDR1-FR2-CDR2-FR3-CDR3-FR4-

MDSQAQVLMLLLLWVSGTCGDIVMSQSPSSLAVSVEEKVNMSCKSSQSLLYSRNQKNYLAWYQQKPGQSPKLLIY

WASTRESGVPDRFTGSGAGTDFTLTISSVKAEDLAVYYCQQYYTYPFTFGSGTKLEIK

FIG. 10

Heavy chain: DNA sequence (SEQ ID NO: 43)

Signal sequence-FR1-CDR1-FR2-CDR2-FR3-CDR3-FR4

ATGAAAGTGTTGAGTCTGTTGTACCTGTTGACAGCCATTCCTGGTATCCTGTCTGATGTACAGCTTCAGGAGTCA

GGACCTGGCCTCGTGAAACCTTCTCAGTCTCTGTCTCTCACCTGCTCTGTCACTGGCTACTCCATCACCAGTGGT

TATTACTGGAACTGGATCCGGCAGTTTCCAGGAAACAAACTGGAATGGATGGGCTACATAAGCTACGACGGTAGC

AATAACTACAACCCATCTCTCAAAAATCGAATCTCCATCACTCGTGACACATATAAGAAGCAGTTTTTCCTGAAG

TTGAATTCTGTGACTACTGAGGACACAGCCACATATTACTGTGCAAGGGGGGGCTGATTACTACGGTAATACCTAC

TTCTACTTCGATGTCTGGGGCGCAGGGACCACGGTCACCGTCTCCTCA

Heavy chain: Amino acid sequence (SEQ ID NO: 44)

Signal peptide-FR1-CDR1-FR2-CDR2-FR3-CDR3-FR4

MKVLSLLYLLTAIPGILSDVQLQESGPGLVKPSQSLSLTCSVTGYSITSGYYWNWIRQFPGNKLEWMGYISYDGS

NNYNPSLKNRISITRDTYKKQFFLKLNSVTTEDTATYYCARGADYYGNTYFYFDVWGAGTTVTVSS

SEQUENCE LISTING

<160> NUMBER OF SEQ ID NOS: 46

<210> SEQ ID NO 1
<211> LENGTH: 604
<212> TYPE: PRT
<213> ORGANISM: Artificial Sequence
<220> FEATURE:
<223> OTHER INFORMATION: human cyclooxygenase 2 protein

<400> SEQUENCE: 1

```
Met Leu Ala Arg Ala Leu Leu Leu Cys Ala Val Leu Ala Leu Ser His
1               5                   10                  15

Thr Ala Asn Pro Cys Cys Ser His Pro Cys Gln Asn Arg Gly Val Cys
                20                  25                  30

Met Ser Val Gly Phe Asp Gln Tyr Lys Cys Asp Cys Thr Arg Thr Gly
            35                  40                  45

Phe Tyr Gly Glu Asn Cys Ser Thr Pro Glu Phe Leu Thr Arg Ile Lys
        50                  55                  60

Leu Phe Leu Lys Pro Thr Pro Asn Thr Val His Tyr Ile Leu Thr His
65                  70                  75                  80

Phe Lys Gly Phe Trp Asn Val Val Asn Asn Ile Pro Phe Leu Arg Asn
                85                  90                  95

Ala Ile Met Ser Tyr Val Leu Thr Ser Arg Ser His Leu Ile Asp Ser
                100                 105                 110

Pro Pro Thr Tyr Asn Ala Asp Tyr Gly Tyr Lys Ser Trp Glu Ala Phe
            115                 120                 125

Ser Asn Leu Ser Tyr Tyr Thr Arg Ala Leu Pro Pro Val Pro Asp Asp
        130                 135                 140

Cys Pro Thr Pro Leu Gly Val Lys Gly Lys Lys Gln Leu Pro Asp Ser
145                 150                 155                 160

Asn Glu Ile Val Glu Lys Leu Leu Leu Arg Arg Lys Phe Ile Pro Asp
                165                 170                 175

Pro Gln Gly Ser Asn Met Met Phe Ala Phe Phe Ala Gln His Phe Thr
                180                 185                 190

His Gln Phe Phe Lys Thr Asp His Lys Arg Gly Pro Ala Phe Thr Asn
            195                 200                 205

Gly Leu Gly His Gly Val Asp Leu Asn His Ile Tyr Gly Glu Thr Leu
        210                 215                 220

Ala Arg Gln Arg Lys Leu Arg Leu Phe Lys Asp Gly Lys Met Lys Tyr
225                 230                 235                 240

Gln Ile Ile Asp Gly Glu Met Tyr Pro Pro Thr Val Lys Asp Thr Gln
                245                 250                 255

Ala Glu Met Ile Tyr Pro Pro Gln Val Pro Glu His Leu Arg Phe Ala
            260                 265                 270

Val Gly Gln Glu Val Phe Gly Leu Val Pro Gly Leu Met Met Tyr Ala
        275                 280                 285

Thr Ile Trp Leu Arg Glu His Asn Arg Val Cys Asp Val Leu Lys Gln
    290                 295                 300

Glu His Pro Glu Trp Gly Asp Glu Gln Leu Phe Gln Thr Ser Arg Leu
305                 310                 315                 320

Ile Leu Ile Gly Glu Thr Ile Lys Ile Val Ile Glu Asp Tyr Val Gln
                325                 330                 335

His Leu Ser Gly Tyr His Phe Lys Leu Lys Phe Asp Pro Glu Leu Leu
            340                 345                 350

Phe Asn Lys Gln Phe Gln Tyr Gln Asn Arg Ile Ala Ala Glu Phe Asn
```

-continued

```
                355                 360                 365

Thr Leu Tyr His Trp His Pro Leu Leu Pro Asp Thr Phe Gln Ile His
    370                 375                 380

Asp Gln Lys Tyr Asn Tyr Gln Gln Phe Ile Tyr Asn Asn Ser Ile Leu
385                 390                 395                 400

Leu Glu His Gly Ile Thr Gln Phe Val Glu Ser Phe Thr Arg Gln Ile
                405                 410                 415

Ala Gly Arg Val Ala Gly Gly Arg Asn Val Pro Pro Ala Val Gln Lys
                420                 425                 430

Val Ser Gln Ala Ser Ile Asp Gln Ser Arg Gln Met Lys Tyr Gln Ser
                435                 440                 445

Phe Asn Glu Tyr Arg Lys Arg Phe Met Leu Lys Pro Tyr Glu Ser Phe
    450                 455                 460

Glu Glu Leu Thr Gly Glu Lys Glu Met Ser Ala Glu Leu Glu Ala Leu
465                 470                 475                 480

Tyr Gly Asp Ile Asp Ala Val Glu Leu Tyr Pro Ala Leu Leu Val Glu
                485                 490                 495

Lys Pro Arg Pro Asp Ala Ile Phe Gly Glu Thr Met Val Glu Val Gly
                500                 505                 510

Ala Pro Phe Ser Leu Lys Gly Leu Met Gly Asn Val Ile Cys Ser Pro
                515                 520                 525

Ala Tyr Trp Lys Pro Ser Thr Phe Gly Gly Glu Val Gly Phe Gln Ile
    530                 535                 540

Ile Asn Thr Ala Ser Ile Gln Ser Leu Ile Cys Asn Asn Val Lys Gly
545                 550                 555                 560

Cys Pro Phe Thr Ser Phe Ser Val Pro Asp Pro Glu Leu Ile Lys Thr
                565                 570                 575

Val Thr Ile Asn Ala Ser Ser Ser Arg Ser Gly Leu Asp Asp Ile Asn
                580                 585                 590

Pro Thr Val Leu Leu Lys Glu Arg Ser Thr Glu Leu
    595                 600
```

<210> SEQ ID NO 2
<211> LENGTH: 9
<212> TYPE: PRT
<213> ORGANISM: Artificial Sequence
<220> FEATURE:
<223> OTHER INFORMATION: Epitope for S565 acetylated COX-2
<220> FEATURE:
<221> NAME/KEY: MISC_FEATURE
<222> LOCATION: (4)..(4)
<223> OTHER INFORMATION: Xaa is acetylated serine

<400> SEQUENCE: 2

```
Pro Phe Thr Xaa Phe Ser Val Pro Asp
1               5
```

<210> SEQ ID NO 3
<211> LENGTH: 13
<212> TYPE: PRT
<213> ORGANISM: Artificial Sequence
<220> FEATURE:
<223> OTHER INFORMATION: Epitope for S565 acetylated COX-2
<220> FEATURE:
<221> NAME/KEY: MISC_FEATURE
<222> LOCATION: (4)..(4)
<223> OTHER INFORMATION: Xaa is an acetylated serine

<400> SEQUENCE: 3

```
Pro Phe Thr Xaa Phe Ser Val Pro Asp Pro Glu Leu Ile
```

-continued

```
1               5                    10

<210> SEQ ID NO 4
<211> LENGTH: 11
<212> TYPE: PRT
<213> ORGANISM: Artificial Sequence
<220> FEATURE:
<223> OTHER INFORMATION: Epitope for S565 acetylated COX-2
<220> FEATURE:
<221> NAME/KEY: MISC_FEATURE
<222> LOCATION: (6)..(6)
<223> OTHER INFORMATION: Xaa is is an acetylated serine

<400> SEQUENCE: 4

Gly Cys Pro Phe Thr Xaa Phe Ser Val Pro Asp
1               5                    10

<210> SEQ ID NO 5
<211> LENGTH: 16
<212> TYPE: PRT
<213> ORGANISM: Artificial Sequence
<220> FEATURE:
<223> OTHER INFORMATION: CDR-L1 of 9F7-2

<400> SEQUENCE: 5

Arg Ser Ser Gln Ser Ile Val His Arg Asn Gly Phe Thr Tyr Leu Glu
1               5                    10                   15

<210> SEQ ID NO 6
<211> LENGTH: 7
<212> TYPE: PRT
<213> ORGANISM: Artificial Sequence
<220> FEATURE:
<223> OTHER INFORMATION: CDR-L2 of 9F7-2

<400> SEQUENCE: 6

Gln Val Ser Asn Arg Phe Ser
1               5

<210> SEQ ID NO 7
<211> LENGTH: 9
<212> TYPE: PRT
<213> ORGANISM: Artificial Sequence
<220> FEATURE:
<223> OTHER INFORMATION: CDR-L3 of 9F7-2

<400> SEQUENCE: 7

Phe Gln Gly Ser His Val Pro Pro Thr
1               5

<210> SEQ ID NO 8
<211> LENGTH: 5
<212> TYPE: PRT
<213> ORGANISM: Artificial Sequence
<220> FEATURE:
<223> OTHER INFORMATION: CDR-H1 of 9F7-2

<400> SEQUENCE: 8

Asp Tyr Leu Leu Gly
1               5

<210> SEQ ID NO 9
<211> LENGTH: 16
<212> TYPE: PRT
<213> ORGANISM: Artificial Sequence
<220> FEATURE:
<223> OTHER INFORMATION: CDR-H2 of 9F7-2
```

```
<400> SEQUENCE: 9

Asp Ile Tyr Pro Gly Gly Thr Tyr Ile Lys Tyr Asn Glu Lys Phe Lys
1               5                   10                  15

<210> SEQ ID NO 10
<211> LENGTH: 9
<212> TYPE: PRT
<213> ORGANISM: Artificial Sequence
<220> FEATURE:
<223> OTHER INFORMATION: CDR-H3 of 9F7-2

<400> SEQUENCE: 10

Gly Arg Asn Asp Glu Lys Gly Asp Tyr
1               5

<210> SEQ ID NO 11
<211> LENGTH: 112
<212> TYPE: PRT
<213> ORGANISM: Artificial Sequence
<220> FEATURE:
<223> OTHER INFORMATION: Light chain variable region of 9F7-2

<400> SEQUENCE: 11

Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Ser Ile Val His Arg
                20                  25                  30

Asn Gly Phe Thr Tyr Leu Glu Trp Tyr Leu Gln Lys Pro Gly Gln Ser
            35                  40                  45

Pro Lys Leu Leu Ile Tyr Gln Val Ser Asn Arg Phe Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Val Pro Pro Thr Phe Gly Gly Gly Thr Lys Leu Glu Ile Lys
                100                 105                 110

<210> SEQ ID NO 12
<211> LENGTH: 118
<212> TYPE: PRT
<213> ORGANISM: Artificial Sequence
<220> FEATURE:
<223> OTHER INFORMATION: Heavy chain variable region of 9F7-2

<400> SEQUENCE: 12

Gln Val Gln Leu Gln Gln Ser Gly Ala Glu Leu Val Arg Pro Gly Thr
1               5                   10                  15

Ser Val Lys Ile Ser Cys Lys Ala Ser Gly Tyr Thr Phe Thr Asp Tyr
                20                  25                  30

Leu Leu Gly Trp Val Lys Gln Arg Pro Gly His Gly Leu Glu Trp Ile
            35                  40                  45

Gly Asp Ile Tyr Pro Gly Gly Thr Tyr Ile Lys Tyr Asn Glu Lys Phe
        50                  55                  60

Lys Gly Lys Ala Thr Leu Thr Ala Asp Thr Ser Ser Ser Thr Ala Tyr
65                  70                  75                  80

Met Gln Leu Ser Ser Leu Thr Ser Glu Asp Ser Ala Val Tyr Phe Cys
                85                  90                  95

Ala Arg Gly Arg Asn Asp Glu Lys Gly Asp Tyr Trp Gly Gln Gly Thr
                100                 105                 110
```

Ser Val Thr Val Ser Ser
        115

<210> SEQ ID NO 13
<211> LENGTH: 48
<212> TYPE: DNA
<213> ORGANISM: Artificial Sequence
<220> FEATURE:
<223> OTHER INFORMATION: CDR-L1 of 9F7-2

<400> SEQUENCE: 13
agatctagtc agagcattgt acatcgtaat ggattcacct acttagaa                        48

<210> SEQ ID NO 14
<211> LENGTH: 21
<212> TYPE: DNA
<213> ORGANISM: Artificial Sequence
<220> FEATURE:
<223> OTHER INFORMATION: CDR-L2 of 9F7-2

<400> SEQUENCE: 14
caagtttcca accgattttc t                                                     21

<210> SEQ ID NO 15
<211> LENGTH: 27
<212> TYPE: DNA
<213> ORGANISM: Artificial Sequence
<220> FEATURE:
<223> OTHER INFORMATION: CDR-L3 of 9F7-2

<400> SEQUENCE: 15
tttcagggtt cacatgttcc tccgaca                                              27

<210> SEQ ID NO 16
<211> LENGTH: 15
<212> TYPE: DNA
<213> ORGANISM: Artificial Sequence
<220> FEATURE:
<223> OTHER INFORMATION: CDR-H1 of 9F7-2

<400> SEQUENCE: 16
gactacttac taggt                                                           15

<210> SEQ ID NO 17
<211> LENGTH: 51
<212> TYPE: DNA
<213> ORGANISM: Artificial Sequence
<220> FEATURE:
<223> OTHER INFORMATION: CDR-H2 of 9F7-2

<400> SEQUENCE: 17
gatatttacc ctggaggtac ttatattaag tacaatgaga agttcaaggg c                    51

<210> SEQ ID NO 18
<211> LENGTH: 27
<212> TYPE: DNA
<213> ORGANISM: Artificial Sequence
<220> FEATURE:
<223> OTHER INFORMATION: CDR-H3 of 9F7-2

<400> SEQUENCE: 18
gggaggaacg acgagaaggg ggactac                                              27

<210> SEQ ID NO 19
<211> LENGTH: 336

<212> TYPE: DNA
<213> ORGANISM: Artificial Sequence
<220> FEATURE:
<223> OTHER INFORMATION: Light chain variable region of 9F7-2

<400> SEQUENCE: 19

```
gatgttttga tgacccaaac tccactctcc ctgcctgtca gtcttggaga tcaagcctcc      60
atctcttgca gatctagtca gagcattgta catcgtaatg gattcaccta cttagaatgg     120
tacctgcaga aaccaggcca gtctccaaag ctcctgatct accaagtttc caaccgattt     180
tctggggtcc cagacaggtt cagtggcagt ggatcaggga cagatttcac actcaagatc     240
agcagagtgg aggctgagga tctgggagtt tattactgct ttcaggttc acatgttcct      300 ccgacattcg gtggaggcac caagctggaa atcaaa                              336
```

<210> SEQ ID NO 20
<211> LENGTH: 354
<212> TYPE: DNA
<213> ORGANISM: Artificial Sequence
<220> FEATURE:
<223> OTHER INFORMATION: Heavy chain variable region of 9F7-2

<400> SEQUENCE: 20

```
caggtccagc tgcagcagtc tggagctgag ctggtaagac ctgggacttc agtgaagata      60
tcctgcaagg cttctggcta caccttcact gactacttac taggttgggt aaagcagagg     120
cctggacatg gacttgagtg gattggagat atttaccctg gaggtactta tattaagtac     180
aatgagaagt tcaagggcaa ggccacactg actgcagaca tcctccag cactgcctac      240 atgcaactca gtagcctgac atctgaggac tctgctgtct acttctgtgc aagagggagg     300
aacgacgaga aggggggacta ctggggtcaa ggaacctcag tcaccgtctc ctca          354
```

<210> SEQ ID NO 21
<211> LENGTH: 16
<212> TYPE: PRT
<213> ORGANISM: Artificial Sequence
<220> FEATURE:
<223> OTHER INFORMATION: CDR-L1 of 44C7C8

<400> SEQUENCE: 21

```
Lys Ser Ser Gln Ser Leu Leu Tyr Ser Arg Asn Gln Lys Asn Tyr Leu
1               5                   10                  15
```

<210> SEQ ID NO 22
<211> LENGTH: 7
<212> TYPE: PRT
<213> ORGANISM: Artificial Sequence
<220> FEATURE:
<223> OTHER INFORMATION: CDR-L2 of 44C7C8

<400> SEQUENCE: 22

```
Trp Ala Ser Thr Arg Glu Ser
1               5
```

<210> SEQ ID NO 23
<211> LENGTH: 9
<212> TYPE: PRT
<213> ORGANISM: Artificial Sequence
<220> FEATURE:
<223> OTHER INFORMATION: CDR-L3 of 44C7C8

<400> SEQUENCE: 23

```
Gln Gln Tyr Tyr Thr Tyr Pro Phe Thr
1               5
```

```
<210> SEQ ID NO 24
<211> LENGTH: 6
<212> TYPE: PRT
<213> ORGANISM: Artificial Sequence
<220> FEATURE:
<223> OTHER INFORMATION: CDR-H1 of 44C7C8

<400> SEQUENCE: 24

Ser Gly Tyr Tyr Trp Asn
1               5

<210> SEQ ID NO 25
<211> LENGTH: 16
<212> TYPE: PRT
<213> ORGANISM: Artificial Sequence
<220> FEATURE:
<223> OTHER INFORMATION: CDR-H2 of 44C7C8

<400> SEQUENCE: 25

Tyr Ile Ser Tyr Asp Gly Ser Asn Asn Tyr Asn Pro Ser Leu Lys Asn
1               5                   10                  15

<210> SEQ ID NO 26
<211> LENGTH: 14
<212> TYPE: PRT
<213> ORGANISM: Artificial Sequence
<220> FEATURE:
<223> OTHER INFORMATION: CDR-H3 of 44C7C8

<400> SEQUENCE: 26

Gly Ala Asp Tyr Tyr Gly Asn Thr Tyr Phe Tyr Phe Asp Val
1               5                   10

<210> SEQ ID NO 27
<211> LENGTH: 113
<212> TYPE: PRT
<213> ORGANISM: Artificial Sequence
<220> FEATURE:
<223> OTHER INFORMATION: Light chain variable region of 44C7C8

<400> SEQUENCE: 27

Asp Ile Val Met Ser Gln Ser Pro Ser Ser Leu Ala Val Ser Val Glu
1               5                   10                  15

Glu Lys Val Asn Met Ser Cys Lys Ser Ser Gln Ser Leu Leu Tyr Ser
            20                  25                  30

Arg Asn Gln Lys Asn Tyr Leu Ala Trp Tyr Gln Gln Lys Pro Gly Gln
        35                  40                  45

Ser Pro Lys Leu Leu Ile Tyr Trp Ala Ser Thr Arg Glu Ser Gly Val
    50                  55                  60

Pro Asp Arg Phe Thr Gly Ser Gly Ala Gly Thr Asp Phe Thr Leu Thr
65                  70                  75                  80

Ile Ser Ser Val Lys Ala Glu Asp Leu Ala Val Tyr Tyr Cys Gln Gln
                85                  90                  95

Tyr Tyr Thr Tyr Pro Phe Thr Phe Gly Ser Gly Thr Lys Leu Glu Ile
            100                 105                 110

Lys

<210> SEQ ID NO 28
<211> LENGTH: 123
<212> TYPE: PRT
<213> ORGANISM: Artificial Sequence
<220> FEATURE:
```

<223> OTHER INFORMATION: Heavy chain variable region of 44C7C8

<400> SEQUENCE: 28

Asp Val Gln Leu Gln Glu Ser Gly Pro Gly Leu Val Lys Pro Ser Gln
1               5                   10                  15

Ser Leu Ser Leu Thr Cys Ser Val Thr Gly Tyr Ser Ile Thr Ser Gly
            20                  25                  30

Tyr Tyr Trp Asn Trp Ile Arg Gln Phe Pro Gly Asn Lys Leu Glu Trp
        35                  40                  45

Met Gly Tyr Ile Ser Tyr Asp Gly Ser Asn Asn Tyr Asn Pro Ser Leu
    50                  55                  60

Lys Asn Arg Ile Ser Ile Thr Arg Asp Thr Tyr Lys Lys Gln Phe Phe
65                  70                  75                  80

Leu Lys Leu Asn Ser Val Thr Thr Glu Asp Thr Ala Thr Tyr Tyr Cys
                85                  90                  95

Ala Arg Gly Ala Asp Tyr Tyr Gly Asn Thr Tyr Phe Tyr Phe Asp Val
            100                 105                 110

Trp Gly Ala Gly Thr Thr Val Thr Val Ser Ser
        115                 120

<210> SEQ ID NO 29
<211> LENGTH: 51
<212> TYPE: DNA
<213> ORGANISM: Artificial Sequence
<220> FEATURE:
<223> OTHER INFORMATION: CDR-L1 of 44C7C8

<400> SEQUENCE: 29
aagtccagtc agagcctttt atatagtaga aatcaaaaga actacttggc c                51

<210> SEQ ID NO 30
<211> LENGTH: 21
<212> TYPE: DNA
<213> ORGANISM: Artificial Sequence
<220> FEATURE:
<223> OTHER INFORMATION: CDR-L2 of 44C7C8

<400> SEQUENCE: 30
tgggcatcca ctagggaatc t                                                  21

<210> SEQ ID NO 31
<211> LENGTH: 27
<212> TYPE: DNA
<213> ORGANISM: Artificial Sequence
<220> FEATURE:
<223> OTHER INFORMATION: CDR-L3 of 44C7C8

<400> SEQUENCE: 31
cagcaatatt atacctatcc attcacg                                            27

<210> SEQ ID NO 32
<211> LENGTH: 15
<212> TYPE: DNA
<213> ORGANISM: Artificial Sequence
<220> FEATURE:
<223> OTHER INFORMATION: CDR-H1 of 44C7C8

<400> SEQUENCE: 32
gactacttac taggt                                                         15

<210> SEQ ID NO 33
<211> LENGTH: 51

-continued

```
<212> TYPE: DNA
<213> ORGANISM: Artificial Sequence
<220> FEATURE:
<223> OTHER INFORMATION: CDR-H2 of 44C7C8

<400> SEQUENCE: 33
gatatttacc ctggaggtac ttatattaag tacaatgaga agttcaaggg c        51

<210> SEQ ID NO 34
<211> LENGTH: 27
<212> TYPE: DNA
<213> ORGANISM: Artificial Sequence
<220> FEATURE:
<223> OTHER INFORMATION: CDR-H3 of 44C7C8

<400> SEQUENCE: 34
gggaggaacg acgagaaggg ggactac                                   27

<210> SEQ ID NO 35
<211> LENGTH: 339
<212> TYPE: DNA
<213> ORGANISM: Artificial Sequence
<220> FEATURE:
<223> OTHER INFORMATION: Light chain variable region of 44C7C8

<400> SEQUENCE: 35
gacattgtga tgtcacagtc tccatcctcc ctagctgtgt cagttgaaga gaaggttaat   60
atgagctgca agtccagtca gagccttta tatagtagaa atcaaaagaa ctacttggcc   120
tggtaccagc agaaaccagg gcagtctcct aaactactga tttactgggc atccactagg   180
gaatctgggg tccctgatcg cttcacaggc agtggagctg ggacagattt cactctcacc   240
atcagcagtg tgaaggctga agacctggca gtttattact gtcagcaata ttatacctat   300
ccattcacgt tcggctcggg gacaaagttg gaaataaaa                         339

<210> SEQ ID NO 36
<211> LENGTH: 369
<212> TYPE: DNA
<213> ORGANISM: Artificial Sequence
<220> FEATURE:
<223> OTHER INFORMATION: Heavy chain variable region of 44C7C8

<400> SEQUENCE: 36
gatgtacagc ttcaggagtc aggacctggc ctcgtgaaac cttctcagtc tctgtctctc   60
acctgctctg tcactggcta ctccatcacc agtggttatt actggaactg gatccggcag   120
tttccaggaa acaaactgga atggatgggc tacataagct acgacggtag caataactac   180
aacccatctc tcaaaaatcg aatctccatc actcgtgaca catataagaa gcagttttc   240 ctgaagttga attctgtgac tactgaggac acagccacat attactgtgc aaggggggct   300
gattactacg gtaatacct cttctactc gatgtctggg cgcagggac cacggtcacc   360 gtctcctca                                                          369

<210> SEQ ID NO 37
<211> LENGTH: 393
<212> TYPE: DNA
<213> ORGANISM: Artificial Sequence
<220> FEATURE:
<223> OTHER INFORMATION: Light chain variable region(9F7-2)

<400> SEQUENCE: 37
atgaagttgc ctgttaggct gttggtgctg atgttctgga ttcctgcttc cagatgtgat   60
```

```
gttttgatga cccaaactcc actctccctg cctgtcagtc ttggagatca agcctccatc        120
tcttgcagat ctagtcagag cattgtacat cgtaatggat tcacctactt agaatggtac        180
ctgcagaaac caggccagtc tccaaagctc ctgatctacc aagtttccaa ccgattttct        240
ggggtcccag acaggttcag tggcagtgga tcaggacag atttcacact caagatcagc        300
agagtggagg ctgaggatct gggagtttat tactgctttc agggttcaca tgttcctccg        360
acattcggtg gaggcaccaa gctggaaatc aaa                                     393
```

```
<210> SEQ ID NO 38
<211> LENGTH: 131
<212> TYPE: PRT
<213> ORGANISM: Artificial Sequence
<220> FEATURE:
<223> OTHER INFORMATION: Light chain variable region(9F7-2)

<400> SEQUENCE: 38

Met Lys Leu Pro Val Arg Leu Leu Val Leu Met Phe Trp Ile Pro Ala
1               5                   10                  15

Ser Arg Cys Asp Val Leu Met Thr Gln Thr Pro Leu Ser Leu Pro Val
            20                  25                  30

Ser Leu Gly Asp Gln Ala Ser Ile Ser Cys Arg Ser Ser Gln Ser Ile
        35                  40                  45

Val His Arg Asn Gly Phe Thr Tyr Leu Glu Trp Tyr Leu Gln Lys Pro
    50                  55                  60

Gly Gln Ser Pro Lys Leu Leu Ile Tyr Gln Val Ser Asn Arg Phe Ser
65                  70                  75                  80

Gly Val Pro Asp Arg Phe Ser Gly Ser Gly Ser Gly Thr Asp Phe Thr
                85                  90                  95

Leu Lys Ile Ser Arg Val Glu Ala Glu Asp Leu Gly Val Tyr Tyr Cys
            100                 105                 110

Phe Gln Gly Ser His Val Pro Pro Thr Phe Gly Gly Gly Thr Lys Leu
        115                 120                 125

Glu Ile Lys
    130
```

```
<210> SEQ ID NO 39
<211> LENGTH: 411
<212> TYPE: DNA
<213> ORGANISM: Artificial Sequence
<220> FEATURE:
<223> OTHER INFORMATION: Heavy chain variable region(9F7-2)

<400> SEQUENCE: 39
atggaatgga gcggggtctt tatctttctc ttgtcagtca ctgcagatgt ccactcccag         60
gtccagctgc agcagtctgg agctgagctg gtaagacctg ggacttcagt gaagatatcc        120
tgcaaggctt ctggctacac cttcactgac tacttactag gttgggtaaa gcagaggcct        180
ggacatggac ttgagtggat tggagatatt taccctggag gtacttatat taagtacaat        240
gagaagttca agggcaaggc cacactgact gcagacacat cctccagcac tgcctacatg        300
caactcagta gcctgacatc tgaggactct gctgtctact tctgtgcaag agggaggaac        360
gacgagaagg gggactactg gggtcaagga acctcagtca ccgtctcctc a                 411
```

```
<210> SEQ ID NO 40
<211> LENGTH: 137
<212> TYPE: PRT
<213> ORGANISM: Artificial Sequence
<220> FEATURE:
```

<223> OTHER INFORMATION: Heavy chain variable region(9F7-2)

<400> SEQUENCE: 40

```
Met Glu Trp Ser Gly Val Phe Ile Phe Leu Leu Ser Val Thr Ala Asp
1               5                   10                  15

Val His Ser Gln Val Gln Leu Gln Gln Ser Gly Ala Glu Leu Val Arg
            20                  25                  30

Pro Gly Thr Ser Val Lys Ile Ser Cys Lys Ala Ser Gly Tyr Thr Phe
        35                  40                  45

Thr Asp Tyr Leu Leu Gly Trp Val Lys Gln Arg Pro Gly His Gly Leu
    50                  55                  60

Glu Trp Ile Gly Asp Ile Tyr Pro Gly Gly Thr Tyr Ile Lys Tyr Asn
65                  70                  75                  80

Glu Lys Phe Lys Gly Lys Ala Thr Leu Thr Ala Asp Thr Ser Ser Ser
                85                  90                  95

Thr Ala Tyr Met Gln Leu Ser Ser Leu Thr Ser Glu Asp Ser Ala Val
            100                 105                 110

Tyr Phe Cys Ala Arg Gly Arg Asn Asp Glu Lys Gly Asp Tyr Trp Gly
        115                 120                 125

Gln Gly Thr Ser Val Thr Val Ser Ser
    130                 135
```

<210> SEQ ID NO 41
<211> LENGTH: 399
<212> TYPE: DNA
<213> ORGANISM: Artificial Sequence
<220> FEATURE:
<223> OTHER INFORMATION: Light chain variable region(44C7C8)

<400> SEQUENCE: 41

```
atggattcac aggcccaggt tcttatgtta ctgctgctat gggtatctgg tacctgtggg      60
gacattgtga tgtcacagtc tccatcctcc ctagctgtgt cagttgaaga gaaggttaat     120
atgagctgca agtccagtca gagccttta tatagtagaa tcaaaagaa ctacttggcc     180 tggtaccagc agaaaccagg gcagtctcct aaactactga tttactgggc atccactagg     240
gaatctgggg tccctgatcg cttcacaggc agtggagctg ggacagattt cactctcacc     300
atcagcagtg tgaaggctga agacctggca gtttattact gtcagcaata ttatacctat     360
ccattcacgt tcggctcggg gacaaagttg gaaataaaa                           399
```

<210> SEQ ID NO 42
<211> LENGTH: 133
<212> TYPE: PRT
<213> ORGANISM: Artificial Sequence
<220> FEATURE:
<223> OTHER INFORMATION: Light chain variable region(44C7C8)

<400> SEQUENCE: 42

```
Met Asp Ser Gln Ala Gln Val Leu Met Leu Leu Leu Leu Trp Val Ser
1               5                   10                  15

Gly Thr Cys Gly Asp Ile Val Met Ser Gln Ser Pro Ser Ser Leu Ala
            20                  25                  30

Val Ser Val Glu Glu Lys Val Asn Met Ser Cys Lys Ser Ser Gln Ser
        35                  40                  45

Leu Leu Tyr Ser Arg Asn Gln Lys Asn Tyr Leu Ala Trp Tyr Gln Gln
    50                  55                  60

Lys Pro Gly Gln Ser Pro Lys Leu Leu Ile Tyr Trp Ala Ser Thr Arg
65                  70                  75                  80
```

Glu Ser Gly Val Pro Asp Arg Phe Thr Gly Ser Gly Ala Gly Thr Asp
                85                  90                  95

Phe Thr Leu Thr Ile Ser Ser Val Lys Ala Glu Asp Leu Ala Val Tyr
            100                 105                 110

Tyr Cys Gln Gln Tyr Tyr Thr Tyr Pro Phe Thr Phe Gly Ser Gly Thr
        115                 120                 125

Lys Leu Glu Ile Lys
    130

<210> SEQ ID NO 43
<211> LENGTH: 423
<212> TYPE: DNA
<213> ORGANISM: Artificial Sequence
<220> FEATURE:
<223> OTHER INFORMATION: Heavy chain variable region(44C7C8)

<400> SEQUENCE: 43
atgaaagtgt tgagtctgtt gtacctgttg acagccattc ctggtatcct gtctgatgta        60
cagcttcagg agtcaggacc tggcctcgtg aaaccttctc agtctctgtc tctcacctgc       120
tctgtcactg gctactccat caccagtggt tattactgga actggatccg gcagtttcca       180
ggaaacaaac tggaatggat gggctacata agctacgacg gtagcaataa ctacaaccca       240
tctctcaaaa atcgaatctc catcactcgt gacacatata agaagcagtt tttcctgaag       300
ttgaattctg tgactactga ggacacagcc acatattact gtgcaagggg ggctgattac       360
tacggtaata cctacttcta cttcgatgtc tggggcgcag ggaccacggt caccgtctcc       420
tca                                                                     423

<210> SEQ ID NO 44
<211> LENGTH: 141
<212> TYPE: PRT
<213> ORGANISM: Artificial Sequence
<220> FEATURE:
<223> OTHER INFORMATION: Heavy chain variable region(44C7C8)

<400> SEQUENCE: 44

Met Lys Val Leu Ser Leu Leu Tyr Leu Leu Thr Ala Ile Pro Gly Ile
1               5                   10                  15

Leu Ser Asp Val Gln Leu Gln Glu Ser Gly Pro Gly Leu Val Lys Pro
                20                  25                  30

Ser Gln Ser Leu Ser Leu Thr Cys Ser Val Thr Gly Tyr Ser Ile Thr
            35                  40                  45

Ser Gly Tyr Tyr Trp Asn Trp Ile Arg Gln Phe Pro Gly Asn Lys Leu
        50                  55                  60

Glu Trp Met Gly Tyr Ile Ser Tyr Asp Gly Ser Asn Asn Tyr Asn Pro
65                  70                  75                  80

Ser Leu Lys Asn Arg Ile Ser Ile Thr Arg Asp Thr Tyr Lys Lys Gln
                85                  90                  95

Phe Phe Leu Lys Leu Asn Ser Val Thr Thr Glu Asp Thr Ala Thr Tyr
            100                 105                 110

Tyr Cys Ala Arg Gly Ala Asp Tyr Tyr Gly Asn Thr Tyr Phe Tyr Phe
        115                 120                 125

Asp Val Trp Gly Ala Gly Thr Thr Val Thr Val Ser Ser
    130                 135                 140

<210> SEQ ID NO 45
<211> LENGTH: 13

-continued

```
<212> TYPE: PRT
<213> ORGANISM: Artificial Sequence
<220> FEATURE:
<223> OTHER INFORMATION: Control of epitope for COX-2 1

<400> SEQUENCE: 45

Pro Phe Thr Ser Phe Ser Val Pro Asp Pro Glu Leu Ile
1               5                   10

<210> SEQ ID NO 46
<211> LENGTH: 11
<212> TYPE: PRT
<213> ORGANISM: Artificial Sequence
<220> FEATURE:
<223> OTHER INFORMATION: Control of epitope for COX-2 2

<400> SEQUENCE: 46

Gly Cys Pro Phe Thr Ser Phe Ser Val Pro Asp
1               5                   10
```

1

ANTIBODY FOR DETECTING ACETYLATION OF COX2 PROTEIN, AND USES THEREOF

TECHNICAL FIELD

This application is a U.S. National Stage application claiming priority to PCT/KR2020/012647 filed Sep. 18, 2020, which claims the priority of Korean Patent Application No. 10-2019-0116290, filed on Sep. 20, 2019, the entirety of which is a reference of the present application.

The present invention relates to an antibody for detecting acetylation of COX2 protein, and a use thereof, and more specifically, to an antibody that specifically recognizes the acetylation of S565 residue of COX2 protein; and uses thereof for diagnosing neurodegenerative diseases or inflammatory diseases.

CROSS-REFERENCE TO SEQUENCE LISTING

This application contains a sequence listing filed in ST.25 format entitled "321901-1010 Sequence Listing_ST25.txt" created on Jul. 29, 2022, and having a file size of 26,650 bytes. The content of the sequence listing is incorporated herein in its entirety.

BACKGROUND ART

Inflammatory diseases are closely associated with most of diseases, and as a result of basic research in molecular and cellular immunology, methods for diagnosing, treating and preventing diseases based on such immunology have been dramatically changed. One example thereof is the finding of an inducible form of a cyclooxygenase (COX) enzyme. COX protein was first purified in 1976, and constitutive cyclooxygenase (COX) cloned in 1988 was found to act in the synthesis of prostaglandin (PGs) from arachidonic acid (AA). After 3 years of such purification, an inducible enzyme having COX activity was identified and named as COX2, while constitutive COX was named as COX1.

The expression of COX2 is under the regulation of pro-inflammatory cytokines and growth factors. Thus, it has been widely known up to now that COX2 acts on the regulation of both inflammation and cell growth. The COX2 is induced in many tissues and simultaneously shown structurally in the brain and spinal cord, wherein the COX2 acts on neural transmission for pain and fever. The two subtypes of COX are almost similar in structure, but have important differences in selectivity of a substrate and an inhibitor and intracellular positions thereof. Protective prostaglandin (PG), which preserves the shape of the gastric mucosa and maintains a normal renal function in the damaged kidney, is synthesized by COX1. On the other hand, PG synthesized by COX2 in immune cells plays a very important role in the inflammatory process.

COX2 in a normal state is known to mediate various physiological phenomena such as immune responses, but it has been reported that abnormal overexpression or overactivation of COX2 is closely associated with the occurrence and development of various diseases.

Specifically, COX2 is overexpressed in most acute or chronic inflammatory diseases and is very closely associated with the development of diseases (J Neuropathol Exp Neurol, Vol 63, September 2004 pp. 901 910). It has been reported that the expression of COX2 is increased in cancer tissues compared to normal tissues in most human cancers including bladder cancer, breast cancer, colorectal cancer, liver cancer, lung cancer, prostate cancer and stomach cancer. It has been reported that the expression of COX2 is increased in various diseases such as neuroinflammatory diseases, Alzheimer's disease, Parkinson's disease, amyotrophic lateral sclerosis, traumatic brain injury, and ischemia.

In particular, according to the research results of the present inventors, it was confirmed that in the case of neurodegenerative diseases including Alzheimer's disease, the brain expression of the COX2 protein was rapidly increased from a very early stage before observable symptoms of the diseases were expressed (KR10-2019-0068246).

In addition, according to the results of previous studies by the present inventors, it was confirmed that the acetylation of COX2 protein, more specifically, the acetylation at S565 residue of human COX2 protein, was significantly reduced in biological samples from patients with neurodegenerative diseases including Alzheimer's disease (KR10-2018-0127656).

Accordingly, if an antibody capable of specifically detecting the acetylation of S565 residue of the COX2 protein is developed in a biological sample, the antibody may very easily diagnose diseases such as neurodegenerative diseases and inflammatory diseases, in which the acetylation of S565 residue of the COX2 protein is reduced, and may be very effectively used in various research fields, but an antibody capable of specifically detecting the acetylation of the COX2 protein has not yet been developed.

DISCLOSURE

Technical Problem

Therefore, the present inventors have repeated many studies to develop an antibody capable of specifically detecting the acetylation of S565 residue of COX2 protein which was reduced in neurodegenerative diseases, inflammatory diseases, and the like, and as a result, developed an antibody that recognized a specific peptide containing acetylated S565 residue of COX2 protein as an epitope, found that the antibody may be very effectively used for diagnosing neurodegenerative diseases, inflammatory diseases, and the like, and then completed the present invention.

Accordingly, an object of the present invention is to provide an antibody or a functional fragment thereof that specifically recognizes the acetylation of cyclooxygenase 2 (COX2) protein.

Another object of the present invention is to provide a polynucleotide encoding the antibody or the functional fragment thereof.

Another object of the present invention is to provide a vector encoding the polynucleotide.

Another object of the present invention is to provide a host cell transformed with the vector.

Another object of the present invention is to provide a method for preparing an antibody or a functional fragment thereof that specifically recognizes acetylation of cyclooxygenase 2 (COX2) protein, comprising steps of producing a polypeptide including light chain and heavy chain variable regions by culturing cells under a condition in which the polynucleotide is expressed, and recovering the polypeptide from the cells or a culture medium culturing the same.

Another object of the present invention is to provide a composition for diagnosing neurodegenerative diseases comprising the antibody or the functional fragment thereof.

Another object of the present invention is to provide a composition for diagnosing neurodegenerative diseases consisting of the antibody or the functional fragment thereof.

Another object of the present invention is to provide a composition for diagnosing neurodegenerative diseases essentially consisting of the antibody or the functional fragment thereof.

Another object of the present invention is to provide a kit for diagnosing neurodegenerative diseases comprising the antibody or the functional fragment thereof.

Another object of the present invention is to provide a kit for diagnosing neurodegenerative diseases consisting of the antibody or the functional fragment thereof. Another object of the present invention is to provide a kit for diagnosing neurodegenerative diseases essentially consisting of the antibody or the functional fragment thereof.

Another object of the present invention is to provide a composition for diagnosing inflammatory diseases comprising the antibody or the functional fragment thereof.

Another object of the present invention is to provide a composition for diagnosing inflammatory diseases consisting of the antibody or the functional fragment thereof.

Another object of the present invention is to provide a composition for diagnosing inflammatory diseases essentially consisting of the antibody or the functional fragment thereof.

Another object of the present invention is to provide uses of the antibody or the functional fragment thereof for preparing a preparation for diagnosing neurodegenerative diseases.

Yet another object of the present invention is to provide a method for diagnosing neurodegenerative diseases comprising steps of:
- a) obtaining a sample from a subject;
- b) measuring an acetylation level of COX2 protein by adding the antibody or the functional fragment thereof to the sample; and
- c) comparing the acetylation level of the COX2 protein with that of a normal subject, and determining that a subject having a reduced acetylation level of the COX2 protein compared to the normal subject suffers from neurodegenerative diseases.

Another object of the present invention is to provide uses of the antibody or the functional fragment thereof for preparing a preparation for diagnosing inflammatory diseases.

Yet another object of the present invention is to provide a method for diagnosing inflammatory diseases comprising steps of:
- a) obtaining a sample from a subject;
- b) measuring an acetylation level of COX2 protein by adding the antibody or the functional fragment thereof to the sample; and
- c) comparing the acetylation level of the COX2 protein with that of a normal subject, and determining that a subject having a reduced acetylation level of the COX2 protein compared to the normal subject suffers from inflammatory diseases.

Technical Solution

An aspect of the present invention provides an antibody or a functional fragment thereof that specifically recognizes the acetylation of cyclooxygenase 2 (COX2) protein. Another aspect of the present invention provides a polynucleotide encoding the antibody or the functional fragment thereof.

Another aspect of the present invention provides a vector encoding the polynucleotide.

Another aspect of the present invention provides a host cell transformed with the vector.

Another aspect of the present invention provides a method for preparing an antibody or a functional fragment thereof that specifically recognizes acetylation of cyclooxygenase 2 (COX2) protein, comprising steps of producing a polypeptide including light chain and heavy chain variable regions by culturing cells under a condition in which the polynucleotide is expressed, and recovering the polypeptide from the cells or a culture medium culturing the same.

Another aspect of the present invention provides a composition for diagnosing neurodegenerative diseases comprising the antibody or the functional fragment thereof.

In addition, the present invention provides a composition for diagnosing neurodegenerative diseases consisting of the antibody or the functional fragment thereof. In addition, the present invention provides a composition for diagnosing neurodegenerative diseases essentially consisting of the antibody or the functional fragment thereof.

Another aspect of the present invention provides a kit for diagnosing neurodegenerative diseases comprising the antibody or the functional fragment thereof.

In addition, the present invention provides a kit for diagnosing neurodegenerative diseases consisting of the antibody or the functional fragment thereof.

In addition, the present invention provides a kit for diagnosing neurodegenerative diseases essentially consisting of the antibody or the functional fragment thereof.

Another aspect of the present invention provides a composition for diagnosing inflammatory diseases comprising the antibody or the functional fragment thereof.

In addition, the present invention provides a composition for diagnosing inflammatory diseases consisting of the antibody or the functional fragment thereof.

In addition, the present invention provides a composition for diagnosing inflammatory diseases essentially consisting of the antibody or the functional fragment thereof.

Another aspect of the present invention provides uses of the antibody or the functional fragment thereof for preparing a preparation for diagnosing neurodegenerative diseases.

Yet another aspect of the present invention provides a method for diagnosing neurodegenerative diseases comprising steps of:
- a) obtaining a sample from a subject;
- b) measuring an acetylation level of COX2 protein by adding the antibody or the functional fragment thereof to the sample; and
- c) comparing the acetylation level of the COX2 protein with that of a normal subject, and determining that a subject having a reduced acetylation level of the COX2 protein compared to the normal subject suffers from neurodegenerative diseases.

Yet another aspect of the present invention provides uses of the antibody or the functional fragment thereof for preparing a preparation for diagnosing inflammatory diseases.

Yet another aspect of the present invention provides a method for diagnosing inflammatory diseases comprising steps of:
- a) obtaining a sample from a subject;
- b) measuring an acetylation level of COX2 protein by adding the antibody or the functional fragment thereof to the sample; and
- c) comparing the acetylation level of the COX2 protein with that of a normal subject, and determining that a subject having a reduced acetylation level of the COX2 protein compared to the normal subject suffers from inflammatory diseases.

Hereinafter, the present invention will be described in detail.

The present inventors treated [14C]acetyl-CoA to neurons isolated from an Alzheimer's animal model through a previous study (KR10-2018-0127656) and purified COX2 protein to analyze the degree of acetylation, and as a result, confirmed that a low degree of COX2 acetylation was observed in neurons of an Alzheimer's animal model as compared with wild-type mice, and COX2 acetylation was increased in neurons of wild-type mice. In addition, it was confirmed that the acetylation of COX2 protein in the Alzheimer's animal model occurred at serine residue (S565) as a 565-th amino acid, and it was confirmed that the degree of acetylation of the COX2 protein, more specifically, the degree of acetylation of S565 residue of the COX2 protein may be an important diagnostic marker for neurodegenerative diseases including Alzheimer's disease.

Accordingly, in an embodiment of the present invention, an antibody capable of specifically detecting acetylation of the COX2 protein has been developed, and an epitope of the antibody and a sequence of the antibody were specifically confirmed, and it was confirmed that the antibody may detect separately COX2 protein with acetylated S565 residue and a non-acetylated protein with very high specificity. In addition, it is confirmed that the antibody of the present invention may detect whether the COX2 protein is acetylated in animal models and human blood cells and brain tissue to be used as a preparation for diagnosing neurodegenerative diseases including Alzheimer, which has great technical significance.

Accordingly, the present invention provides an antibody or a functional fragment thereof that specifically recognizes the acetylation of cyclooxygenase 2 (COX2) protein.

Unless otherwise defined, all technical and scientific terms used herein have the same meaning as commonly understood by those skilled in the art. The following references provide one skill with general definitions of various DICTIONARY OF BIOLOGY. In addition, the following definitions are provided to aid readers for implementing the present invention.

A single letter (three letters) of amino acids used herein means the following amino acids according to standard abbreviation rules in the field of biochemistry: A(Ala): alanine; C(Cys): cysteine; D(Asp): aspartic acid; E(Glu): glutamic acid; F(Phe): phenylalanine; G(Gly): glycine; H(His): histidine; I(Ile): isoleucine; K(Lys): lysine; L(Leu): leucine; M(Met): methionine; N(Asn): asparagine; O(Ply): pyrrolysine; P(Pro): proline; Q(Gln): glutamine; R(Arg): arginine; S(Ser): serine; T(Thr): threonine; U(Sec): selenocysteine; V(Val): valine; W(Trp): tryptophan; Y(Tyr): Tyrosine.

The term "expression" used herein refers to the generation of proteins or nucleic acids in cells.

In the present invention, the term "host cell" refers to a prokaryotic or eukaryotic cell including heterologous DNA introduced into the cell by any means (e.g., electroshock method, calcium phosphatase precipitation method, microinjection method, transformation method, virus infection, etc.).

In the present invention, "protein" is used interchangeably with "polypeptide", and for example, refers to a polymer of amino acid residues as commonly found in proteins in a natural state.

As used herein, "nucleic acid", "DNA sequence" or "polynucleotide" refers to deoxyribonucleotide or ribonucleotide in single- or double-stranded form. Unless otherwise limited, the 'polynucleotide' also includes known analogs of natural nucleotides that hybridize to nucleic acids in a manner similar to naturally produced nucleotides.

In the present invention, a specific sequence of the COX2 protein is not particularly limited as long as the COX2 protein is COX2 protein known in the art, but preferably human COX2 protein, and an example thereof may refer to a sequence of GeneBank accession No.AAR23927.1, No.AAA58433.1, No. AAA57317.1, and the like, but is not limited thereto. Preferably, in the present invention, the COX2 protein includes a protein consisting of an amino acid sequence represented by SEQ ID NO: 1 or a functional equivalent thereof.

[SEQ ID NO: 1]

```
mlaralllca vlalshtanp ccshpcqnrg vcmsvgfdqy kcdctrtgfy gencstpefl triklflkpt pntvhyilth fkgfwnvvnn ipflrnaims yvltsrshli dspptynady gyksweafsn lsyytralpp vpddcptplg vkgkkqlpds neivekllr rkfipdpqgs nmmfaffaqh fthqffktdh krgpaftngl ghgvdlnhiy getlarqrkl rlfkdgkmky qiidgemypp tvkdtqaemi yppqvpehlr favgqevfgl vpglmmyati wlrehnrvcd vlkqehpewg deqlfqtsrl iligetikiv iedyvqhlsg yhfklkfdpe llfnkqfqyq nriaaefntl yhwhpllpdt fqihdqkyny qqfiynnsil lehgitqfve sftrqiagrv aggrnvppav qkvsqasidq srqmkyqsfn eyrkrfmlkp yesfeeltge kemsaeleal ygdidavely pallvekprp daifgetmve vgapfslkgl mgnvicspay wkpstfggev gfqiintasi qslicnnvkg cpftsfsvpd peliktvtin asssrsgldd inptvllker stel
``` terms used in the present specification. Singleton et al., DICTIONARY OF MICROBIOLOGY AND MOLECULAR BIOLOTY (2d ed. 1994); THE CAMBRIDGE DICTIONARY OF SCIENCE AND TECHNOLOGY (Walker ed., 1988); and Hale & Marham, THE HARPER COLLINS The functional equivalent refers to a polypeptide having sequence homology (that is, identity) of at least 70% or more, preferably 80% or more, more preferably 90% or more with an amino acid sequence (preferably, an amino acid sequence represented by SEQ ID NO: 1) constituting the known COX2 protein. For example, the polypeptide includes polypeptides having sequence homology of 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, and 100%, and refers to a polypeptide that exhibits substantially the same physiological activity as the known COX2 protein (preferably, polypeptide represented by SEQ ID NO: 1) that became the parent. Preferably, the functional equivalent of the COX2 protein in the present invention may be generated as a result of addition, substitution or deletion of a part of the amino acid sequence of SEQ ID NO: 1. The substitution of amino acids is preferably conservative substitution. Examples of the conservative substitution of amino acids present in nature are as follows; aliphatic amino acids (Gly, Ala, Pro), hydrophobic amino acids (Ile, Leu, Val), aromatic amino acids (Phe, Tyr, Trp), acidic amino acids (Asp, Glu), basic amino acids (His, Lys, Arg, Gln, Asn) and sulfur-containing amino acids (Cys, Met). In addition, the functional equivalent of the COX2 protein includes a variant in which some of amino acids are deleted from the amino acid sequence of the COX2 protein. The deletion or substitution of the amino acids is preferably positioned in a region not directly related to the physiological activity of COX2. In addition, the deletion of the amino acids is preferably positioned at a portion not directly involved in the physiological activity of COX2. Further, the functional equivalent of the COX2 protein includes variants in which several amino acids are added at both ends of the amino acid sequence of COX2 or in the sequence. In addition, the range of the functional equivalent of the present invention includes polypeptide derivatives in which some chemical structures of the polypeptide are modified while maintaining the basic backbone of COX2 and its physiological activity. For example, the functional equivalent thereof is structural modifications for changing the stability, storage, volatility, solubility or the like of the protein.

In the present specification, sequence homology and homogeneity are defined as a percentage of identical matching residues (amino acid residues or bases) of a candidate sequence for an original sequence after aligning the original sequence (SEQ ID NO: 1 as a preferred example in the case of the amino acid sequence) and the candidate sequence and introducing gaps. If necessary, conservative substitution is not considered as part of sequence homogeneity in order to obtain the maximum percentage sequence homogeneity. Further, in the case of determining homology or homogeneity of protein sequence, an N-terminus, a C-terminus or internal extension, deletion or insertion of the COX2 protein amino acid sequence is not construed as a sequence affecting sequence homology or homogeneity. In addition, the sequence homogeneity may be determined by standard methods generally used to compare similar portions of amino acid sequences of two polypeptides. A computer program such as BLAST or FASTA aligns the two polypeptides for optimal matching of respective amino acids (either along the full-length sequence of one or two sequences, or along the predicted portions of one or two sequences). The program provides a default opening penalty and a default gap penalty and provides a scoring matrix such as PAM250 (standard scoring matrix; Dayhoff et al., in Atlas of Protein Sequence and Structure, vol 5, supp 3, 1978) which may be associated and used together with the computer program. For example, the percentage homogeneity may be calculated as follows. The total number of identical matches is multiplied by 100 and then divided into a sum of the length of a longer sequence in the corresponding matched span and the number of gaps introduced into the longer sequence to align the two sequences.

The heavy and light chains of the antibody are structurally divided into a variable region and a constant region according to the variability of the amino acid sequence. The constant region of the heavy chain consists of 3 or 4 heavy chain constant regions such as CH1, CH2 and CH3 (IgA, IgD and IgG antibodies) and CH4 (IgE and IgM antibodies) depending on a type of antibody, and the light chain consists of one constant region CL. The variable regions of the heavy and light chains each consists of one domain of a heavy chain variable region (VH) or a light chain variable region (VL). The light chain and the heavy chain are linked by one covalent disulfide bond, in which the variable region and the constant region are aligned side by side, and the heavy chains of the two molecules bound to the light chain are linked through two covalent disulfide bonds to form the whole antibody. Since the whole antibody specifically binds to the antigen through the variable regions of the heavy and light chains and the whole antibody consists of a pair of two heavy and light chains (HC/LC), the whole antibody of one molecule has bivalent mono-specificity binding to the same two antigens through two variable regions.

The variable region including a antigen-binding site of the antibody is subdivided into a framework region (FR) with low sequence variability and a complementary determining region (CDR), which is a hypervariable region with high sequence variability. In VH and VL, three CDRs and four FRs are arranged in the order of FR1-CDR1-FR2-CDR2-FR3-CDR3-FR4 in a direction from the N-terminus to the C-terminus, respectively. The CDR with the highest sequence variability within the variable region of the antibody is a site directly binding to the antigen, and is the most important for antigen specificity of the antibody.

In one embodiment, the antibody or its functional fragment of the present invention is an antibody or its functional fragment which specifically recognizes the acetylation of the COX2 protein or its functional equivalent, preferably may be an antibody or its functional fragment that specifically recognizes the acetylation of S565 residue of the COX2 protein represented by SEQ ID NO: 1.

In the present invention, the term 'epitope' refers to a specific region that determines the antigen-antibody reaction specificity in any object to which any antibody specifically binds, and the antibody or its functional fragment of the present invention may be characterized by recognizing a peptide consisting of 9 to 50 amino acids including an amino acid sequence (PFTSacFSVPD) represented by SEQ ID NO: 2 as an epitope.

In addition, the antibody or the functional fragment thereof of the present invention may be characterized in that a PELI sequence is additionally included in the C terminus of the amino acid sequence (PFTSacFSVPD) represented by SEQ ID NO: 2 or a GC sequence is further included in the N terminus.

Preferably, the antibody or the functional fragment thereof of the present invention may recognize a peptide consisting of consecutive 9 to 50 amino acids comprising the amino acid sequence represented by SEQ ID NO: 2 in an amino acid sequence of SEQ ID NO: 1, for example, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 amino acids as an epitope.

More preferably, the antibody or the functional fragment thereof of the present invention may recognize a peptide consisting of consecutive 9 to 15 amino acids comprising the amino acid sequence represented by SEQ ID NO: 2 in the amino acid sequence of SEQ ID NO: 1, for example, 9, 10, 11, 12, 13, 14 or 15 amino acids as an epitope.

Much more preferably, the antibody or the functional fragment thereof of the present invention may recognize a peptide consisting of consecutive 9 to 13 amino acids comprising the amino acid sequence represented by SEQ ID NO: 2 in the amino acid sequence of SEQ ID NO: 1, for example, 9, 10, 11, 12, or 13 amino acids as an epitope.

Most preferably, the antibody or the functional fragment thereof of the present invention may recognize a peptide consisting of an amino acid sequence represented by SEQ ID NO: 3 or SEQ ID NO: 4 as an epitope.

The antibody of the present invention is used in the broadest meaning in the present invention. Specifically, monoclonal antibodies (including monoclonal antibodies and full-length monoclonal antibodies), polyclonal antibodies (polyclonal antibodies), multispecific antibodies (e.g., bispecific antibodies), and antibody fragments (e.g., variable regions and other portions of the antibody that exhibit desired biological activity (e.g., binding to acetylated COX2 protein).

The antibody of the present invention includes all monoclonal antibodies and polyclonal antibodies, preferably monoclonal antibodies, as antibodies in which specific amino acid sequences are included in light and heavy chain CDRs so as to selectively bind to acetylated COX2 protein. In addition, the antibody of the present invention includes all of chimeric antibodies, humanized antibodies, and human antibodies, preferably human antibodies.

The monoclonal antibody of the present invention refers to an antibody obtained from a group of substantially homogeneous antibodies, that is, individual antibodies constituting the group are identical except for possible naturally occurring mutations that may be present in small amounts. The monoclonal antibody very specifically binds to a single antigenic epitope.

In the present invention, the term 'monoclone' or 'monoclonal' indicates obtaining the antibody from a substantially homologous group and representing the characteristics of the antibody, and does not necessarily mean that the antibody needs to be produced by a specific method. For example, a single antibody of the present invention may be prepared by a hybridoma method known in the art, or may be prepared by a recombinant DNA method (see U.S. Pat. No. 4,816,567). In addition, for example, the single antibody may be isolated from a phage antibody library using a technique described in references (see Clackson et al. (1991) Nature 352:624-628 and Marks et al. (1991) J. Mol. Biol. 222:581-597 and Presta (2005) J. Allergy Clin. Immunol. 116:731).

The antibody of the present invention includes specifically a chimeric antibody, and in this case, a part of the heavy and/or light chain is derived from a particular species or identical or homologous to the corresponding sequence of a specific antibody, but other parts thereof may be derived from a different species or may be identical or homologous to the corresponding sequence of another antibody, as long as the antibody of the present invention exhibits preferable biological activity (e.g., selective binding to acetylated COX2) (U.S. Pat. No. 4,816,567).

The humanized antibody is an antibody including sequences of both human and non-human (e.g., mouse, rat) antibodies. In general, the remaining part except for an epitope-binding region (CDR) is a sequence of the human antibody, and the epitope-binding region (CDR) may include a non-human derived sequence. The complete human antibody refers to an antibody including only a human immunoglobulin protein sequence, and may be produced from mice, mouse cells, or hybridomas derived from mouse cells, or produced by a phage display method.

The hybridoma cells may be prepared using methods known in the art.

Specifically, the hybridoma cells may be prepared by a method of selecting of hybridoma by immunizing a peptide including an amino acid sequence represented by SEQ ID NO: 2 as an immunogen and consisting of consecutive 9 to 50 amino acids, preferably a peptide including an amino acid sequence represented by SEQ ID NO: 2 in an amino acid sequence of SEQ ID NO: 1 and consisting of consecutive 9 to 50 amino acids, most preferably a peptide consisting of an amino acid sequence represented by SEQ ID NO: 3 or 4 to an animal, fusing B cells as antibody-producing cells derived from the immunized animal with myeloma cells to prepare hybridoma, and then producing monoclonal antibodies specifically binding to the peptide among them. The immunized animal may be not only a mouse but also animals such as goat, sheep, guinea pig, rat or rabbit.

As a method for immunizing the immunized animal, methods known in the art may be used. For example, in the case of immunizing the mouse, 1 to 100 μg of the immunogen at a time is emulsified with the same amount of physiological saline and/or an antigen adjuvant such as a Freund's adjuvant, and inoculated subcutaneously or intraperitoneally in the abdomen of the immunized animal 2 to 6 times every 2 to 5 weeks. After the immunized animal is immunized, the spleen or lymph node is extracted after 3 to 5 days of the final immunization, and the B cells contained in these tissues are fused to myeloma cells in the presence of a fusion accelerator according to a cell fusion method known in the art. The fusion accelerator may be, for example, a material such as polyethylene glycol (PEG). The myeloma cells may use, for example, mouse-derived cells such as P3U1, NS-1, P3×63.Ag 8.653 and Sp2/0-Ag14, and rat-derived cells such as AG1 and AG2. In addition, the cell fusion method known in the art may be performed by, for example, a method of mixing B cells and myeloma cells in a ratio of 1:1 to 10:1, adding PEG having a molecular weight of 1,000 to 6,000 thereto at a concentration of 10 to 80%, and then incubating the mixture at 30 to 37° C. for 1 to 10 minutes. In addition, the hybridoma producing the monoclonal antibodies that specifically bind to the immunogenic peptide is cultured in a selective medium such as a HAT medium in which only the hybridoma is survivable and may be selected by measuring the antibody activity in a hybridoma culture supernatant using a method such as ELISA and the like. Finally, the hybridoma producing the monoclonal antibodies that specifically bind to the immunogenic peptide may be screened by repeating cloning by a method such as limiting dilution, with respect to, for example, a hybridoma that produces monoclonal antibodies that specifically binds to the immunogenic peptide.

In addition, the monoclonal antibody or the functional fragment thereof provided by the present invention may generate human antibodies and antibody fragments in vitro from an immunoglobulin variable region gene repertoire from unimmunized donors using phage display technology. According to this technique, an antibody variable region gene is cloned in frame into a major or minor coat protein of a filamentous bacteriophage, such as M13 or fd, and a functional antibody fragment is displayed on the surface of a phage particle. Since the filamentous particle contains a single-stranded DNA copy of a phage genome, due to selection based on the functional properties of the antibody, genes encoding an antibody exhibiting these properties are screened. Thus, the phage mimics some properties of B-cells. The phage display may be performed in a variety of formats. A study thereof may refer to a reference [Johnson, Kevin S. and Chiswell, David J. Current Opinion in Structural Biology 3:564-571 (1993)]. Several supply sources of variable region-gene segments may be used for the phage display. In the reference [Clackson et al., Nature, 352:624-628 (1991)], various arrays of anti-oxazolone antibodies were isolated from a small random combination library of variable region genes derived from the spleen of immunized mice. A repertoire of variable region genes from unimmunized human donors was constructed, and technology described in the reference [Marks et al., J. Mol. Biol. 222:581-597 (1991), or Griffith et al., EMBO J. 12:725-734 (1993)] was essentially performed to isolate antibodies to various arrays of antigens (including autoantigens) [see U.S. Pat. Nos. 5,565,332 and 5,573,905].

According to an aspect, the antibody or the functional fragment thereof according to the present invention may include an antibody or a functional fragment thereof comprising an antibody light chain variable region VL having a complementarity determining region (CDR) L1 including an amino acid sequence represented by SEQ ID NO: 5, a complementarity determining region (CDR) L2 including an amino acid sequence represented by SEQ ID NO: 6, and a complementarity determining region (CDR) L3 including an amino acid sequence represented by SEQ ID NO: 7 and an antibody heavy chain variable region VH having a complementarity determining region (CDR) H1 including an amino acid sequence represented by SEQ ID NO: 8, a complementarity determining region (CDR) H2 including an amino acid sequence represented by SEQ ID NO: 9, and a complementarity determining region (CDR) H3 including an amino acid sequence represented by SEQ ID NO: 10; or an antibody or a functional fragment thereof comprising an antibody light chain variable region VL having a complementarity determining region (CDR) L1 including an amino acid sequence represented by SEQ ID NO: 21, a complementarity determining region (CDR) L2 including an amino acid sequence represented by SEQ ID NO: 22, and a complementarity determining region (CDR) L3 including an amino acid sequence represented by SEQ ID NO: 23 and an antibody heavy chain variable region VH having a complementarity determining region (CDR) H1 including an amino acid sequence represented by SEQ ID NO: 24, a complementarity determining region (CDR) H2 including an amino acid sequence represented by SEQ ID NO: 25, and a complementarity determining region (CDR) H3 including an amino acid sequence represented by SEQ ID NO: 26.

According to yet another aspect, the antibody or the functional fragment thereof according to the present invention may include an antibody or a functional fragment thereof comprising a light chain variable region VL including an amino acid sequence represented by SEQ ID NO: 11 and a heavy chain variable region VH including an amino acid sequence represented by SEQ ID NO: 12; or an antibody or a functional fragment thereof comprising a light chain variable region VL including an amino acid sequence represented by SEQ ID NO: 27 and a heavy chain variable region VH including an amino acid sequence represented by SEQ ID NO: 28.

The type of antibody according to the present invention is not specifically limited as long as the antibody specifically recognizes acetylation of the COX2 protein, and as a specific example, the antibody may be selected from the group consisting of IgG, IgA, IgM, IgE and IgD.

In the present invention, the functional fragment of the antibody refers to a fragment of the antibody that maintains the binding force to the acetylated residue of the COX2 protein, and preferably, the fragment has at least 20%, 50%, 70%, 80%, 90%, 95% or 100% or more of the protein affinity of a parent antibody. Specifically, the functional fragment may be in the form of a diabody, Fab, Fab', F(ab)2, F(ab')2, Fv and scFv.

Fragment antigen-binding (Fab) is an antigen-binding fragment of the antibody, and consists of one variable domain and one constant domain of each of the heavy and light chains. F(ab')2 is a fragment produced by hydrolyzing the antibody with pepsin, and has a form in which two Fabs are linked by a disulfide bond at a heavy chain hinge. F(ab') is a monomeric antibody fragment in which a heavy chain hinge is added to Fab separated by reducing the disulfide bond of the F(ab')2 fragment. A variable fragment (Fv) is an antibody fragment consisting of only the variable region of each of the heavy and light chains. A single chain variable fragment (ScFv) is a recombinant antibody fragment in which the heavy chain variable region VH and the light chain variable region VL are linked to each other by a flexible peptide linker. The diabody refers to a fragment in which VH and VL of scFv are linked to each other by a very short linker so as not to bind to each other, but bind to each of VH and VL of another scFv in the same form to form a dimmer.

The antibody or the fragment thereof of the present invention may include conservative amino acid substitutions (referred to as conservative variants of the antibody) that do not substantially alter its biological activity. Such an amino acid substitution may refer to those described above.

In addition, the antibody or the fragment thereof of the present invention described above may be conjugated to an enzyme, a fluorescent material, a radioactive material, or a protein, but is not limited thereto. In addition, methods for conjugating the material to the antibody are well known in the art.

The present invention also provides a polynucleotide encoding the antibody or the functional fragment thereof.

In the present invention, the 'polynucleotide' may be described as an oligonucleotide or nucleic acid, and includes DNA molecules (e.g., cDNA or genomic DNA), RNA molecules (e.g., mRNA), analogs of the DNA or RNA (e.g., peptide nucleic acids and non-naturally occurring nucleotide analogs) produced using nucleotide analogues, and hybrids thereof. The polynucleotide may be single-stranded or double-stranded. The polynucleotide refers to a nucleotide sequence encoding an antibody comprising a heavy chain and a light chain having a CDR configuration or VH and VL configurations specific to acetylated residues of the COX2 protein.

The polynucleotide encoding the antibody or the fragment thereof of the present invention may be obtained by methods well known in the art. For example, based on the DNA sequence or the corresponding amino acid sequence encoding a part or all of the heavy and light chains of the antibody, the polynucleotide may be synthesized using an oligonucleotide synthesis technique well known in the art, for example, a polymerase chain reaction (PCR) method, and the like.

The present invention also provides a vector comprising the polynucleotide.

The 'vector' of the present invention is used for the purpose of replication or expression of the polynucleotide of the present invention for recombinant production of the antibody or the fragment thereof of the present invention, and generally includes one or more of a signal sequence, a replication origin, one or more marker genes, an enhancer element, a promoter and a transcription termination sequence. The vector of the present invention may be preferably an expression vector, more preferably a vector comprising the polynucleotide of the present invention operably linked to a regulatory sequence, for example, a promoter.

A plasmid, a kind of vector, refers to a DNA molecule of a linear or circular double helix to which external polynucleotide fragments may bind. Another form of the vector is viral vectors (e.g., replication defective retroviruses, adenoviruses and adeno-associated viruses), wherein additional DNA fragments may be introduced into the viral genome. Specific vectors may be self-replicated in host cells (e.g., bacterial vectors, including a bacterial origin and episomal mammalian vectors) introduced thereinto. Other vectors (e.g., non-episomal mammalian vectors) are integrated into the genome of the host cell by introduction into the host cell and replicated with the host genome.

In the present invention, the 'vector' may be understood as the same meaning as the 'expression vector', which is a form of vector capable of expressing the polynucleotide. A polynucleotide sequence is "operably linked" to the regulatory sequence when the regulatory sequence affects the expression (e.g., level, timing or position of expression) of the polynucleotide sequence. The regulatory sequence is a sequence that affects the expression (e.g., level, timing or position of expression) of a nucleic acid which is operably linked. The regulatory sequence may have its effect, for example, directly on the regulated nucleic acid or through the action of one or more other molecules (e.g., polypeptides that bind to the regulatory sequence and/or the nucleic acid). The regulatory sequence includes promoters, enhancers, and other expression regulatory elements.

The present invention also provides cells transformed with the vector.

The type of cell of the present invention is not particularly limited as long as the cell may be used to express a polynucleotide encoding the antibody or the fragment thereof included in the expression vector of the present invention. Cells (host cells) transformed with the expression vector according to the present invention may be prokaryotes (e.g., E. coli), eukaryotes (e.g., yeast or other fungi), plant cells (e.g., tobacco or tomato plants), animal cells (e.g., human cells, monkey cells, hamster cells, rat cells, mouse cells, insect cells), or hybridomas derived therefrom. Preferably, the cells may be derived from mammals including humans.

The prokaryotes suitable for the object include gram-negative or gram-positive organisms, for example, Enterobacteriaceae, for example, Escherichia such as E. coli, Enterobacter, Erwinia, Klebsiella, Proteus, Salmonella such as Salmonella typhimurium, Serratia such as Serratia marcescans and Shigella, and Bacilli such as B. subtilis and B. licheniformis, Pseudomonas such as P.aeruginosa, and Streptomyces. The cells of the present invention are not particularly limited as long as the cells can express the vector of the present invention, but preferably E. coli.

Saccharomyces cerevisiae is the most commonly used in eukaryotes as the cell of the present invention. However, many other genera, species and strains are not limited thereto, and can use, for example, Schizosaccharomyces pombe, Kluyveromyces hosts such as K.lactis, K. fragilis (ATCC 12,424), K. bulgaricus (ATCC 16,045), K.wickeramii (ATCC 24,178), K. waltii (ATCC 56,500), K.drosophilarum (ATCC 36,906), K. thermotolerans and K.marxianus; yarrowia (EP 402,226); Pichia pastoris (EP 183,070);

Candida; Trichoderma reesia (EP 244,234); Neurospora crassa; Schwanniomyces such as occidentalis; and filamentous fungi such as neurospora, penicillium, tolypocladium, and Aspergillus such as A. nidulans and A. niger.

The term 'transformation' refers to a modification of a genotype of a host cell by introduction of an exogenous polynucleotide, and means the introduction of the exogenous polynucleotide into a host cell regardless of the method used for the transformation. The exogenous polynucleotide introduced into the host cell may be integrated and maintained or not integrated but maintained into the genome of the host cell, and the present invention includes both.

The recombinant expression vector capable of expressing the antibody or the functional fragment thereof according to the present invention may be introduced into cells for producing the antibody or the fragment thereof and transformed by methods known in the art, but are not limited thereto, for example, transient transfection, microinjection, transduction, cell fusion, calcium phosphate precipitation, liposome-mediated transfection, DEAE dextran-mediated transfection, polybrene-mediated transfection, electroporation, gene gun, and known methods for introducing nucleic acid into cells.

In addition, the cells of the present invention are cultured cells that may be transformed or transfected with the polynucleotide of the present invention or a vector including the same, which may be continuously expressed in the host cell. The recombinant cell refers to a cell transformed or transfected with a polynucleotide to be expressed. The cells of the present invention may also include the polynucleotide of the present invention, but may be cells which are not expressed at a desired level unless introduced into the cells so that the regulatory sequence is operably linked to the polynucleotide.

The cells of the present invention may be cultured in various media. Commercially available media, such as Ham's F1O (Sigma-Aldrich Co., St. Louis, MO), minimal essential media (MEM, Sigma-Aldrich Co.), RPMI-1640 (Sigma-Aldrich Co.), and Dulbecco's modified Eagle's media (DMEM, Sigma-Aldrich Co.), are suitable for culturing the cells. The media may be added with hormones and/or other growth factors, salts, buffers, nucleotides, antibiotics, trace elements and glucose or equivalent energy sources, if necessary.

The present invention provides a method for producing an antibody or a fragment thereof binding to WRS comprising steps of producing a polypeptide comprising light chain and heavy chain variable regions by culturing the cells under conditions in which the polynucleotide is expressed, and recovering the polypeptide from the cells or the culture medium in which the cells are cultured.

The cells of the producing method in the present invention are as described above, and include a polynucleotide encoding the antibody of the present invention. The polypeptide of the producing method may be the antibody or the fragment thereof of the present invention itself, and may be a peptide to which an amino acid sequence other than the antibody or the fragment thereof of the present invention additionally binds.

In this case, the polypeptide may be removed from the antibody or the fragment thereof of the present invention using a method well known to those skilled in the art. The medium compositions and culture conditions of the culturing may vary depending on a type of cell, which may be appropriately selected and controlled by those skilled in the art.

The antibody molecules are accumulated in the cytoplasm of the cell, secreted from the cell, or may be targeted to a periplasm or a supernatant by an appropriate signal sequence, and preferably targeted to the periplasm or the supernatant. In addition, it is preferable to refold the produced antibody molecules using a method well-known to those skilled in the art and have a functional conformation. The recovery of the polypeptide may vary depending on the characteristics of the produced polypeptide and the characteristics of cells, which may be appropriately selected and controlled by those skilled in the art.

The polypeptide may be produced in the cell or in a periplasmic space, or directly secreted into the medium. If the polypeptide is produced in the cell, the cell may be broken to release the protein as a first step. Particulate debris, host cells or lysed fragments are removed, for example, by centrifugation or ultrafiltration. When the antibody is secreted into the medium, the supernatant from such an expression system is generally first concentrated using a commercially available protein concentration filter, such as an Amicon or Millipore Pellicon ultrafiltration unit. A protease inhibitor such as PMSF may be included in any preceding step to inhibit proteolysis, and antibiotics may be included to prevent the growth of incidental contaminants. Antibodies prepared from cells may be purified using, for example, hydroxyapatite chromatography, gel electrophoresis, dialysis and affinity chromatography, and the antibody of the present invention may be purified preferably through affinity chromatography.

Since the antibody or the functional fragment thereof of the present invention specifically binds to an acetylated residue of COX2 protein, more specifically acetylated S565 residue in COX2 protein of SEQ ID NO: 1, for example, the antibody or the functional fragment thereof is useful in diagnostic assay to detect and quantify the expression of acetylated COX2 protein in a specific cell, tissue, or serum.

For this purpose, the antibody or the functional fragment thereof may generally be labeled with a detectable moiety.

For example, the antibody or the functional fragment thereof may be labeled with a radioactive isotope or a fluorescent marker using techniques known in the art. Radioactivity may be measured, for example, by scintillation counting, and fluorescence may be quantified using a fluorometer. Alternatively, various enzyme-substrate markers are available, and examples of the enzyme marker include luciferases such as *drosophila* luciferase and bacterial luciferase (U.S. Pat. No. 4,737,456), luciferin, 2,3-dihydrophthalazindiones, malate dehydrogenase, urase, peroxidase such as horseradish peroxidase (HRPO), alkaline phosphatase, $\beta$-galactosidase, glucoamylase, lysozyme, saccharide oxidase (e.g., glucose oxidase, galactose oxidase, and glucose-6-phosphate dehydrogenase), heterocyclic oxidase (e.g., uricase and xanthine oxidase), lactoperoxidase, microperoxidase and the like. Techniques for conjugating an enzyme to an antibody are, for example, known in the art.

The marker may be indirectly conjugated to the antibody using a variety of known techniques. For example, the antibody may be conjugated to biotin and any markers belonging to three broad categories mentioned above may be conjugated to avidin, and vice versa. Biotin binds selectively to avidin, and accordingly, this marker may be conjugated to the antibody by such an indirect method. Alternatively, in order to achieve indirect conjugation of the marker to the antibody, the antibody may be conjugated with small hapten (e.g., digoxin) and one of the different types of markers mentioned above may be conjugated to an anti-hapten antibody (e.g., an anti-digoxin antibody). Thus, indirect conjugation of the marker to the antibody may be achieved.

The antibody or the functional fragment thereof of the present invention may be used in any known assay method, such as competitive binding assay, direct and indirect sandwich assay, and immunoprecipitation assay.

The antibody or the functional fragment thereof of the present invention may be used in a packaged combination of reagents in a predetermined amount together with a diagnostic kit, i.e., a diagnostic kit for performing diagnostic assay. When the antibody is labeled with the enzyme, the kit may include a substrate and a cofactor required by the enzyme as a substrate precursor to provide a chromophore or fluorophore. In addition, other additives, such as stabilizers, buffers (e.g., blocking buffers or lysis buffers), and the like may also be included. The relative amounts of various reagents may be varied widely to provide concentrations in a solution of the reagents that sufficiently optimize the sensitivity of the assay. The reagents may be generally provided as lyophilized, dry powder with excipients to provide a reagent solution having an appropriate concentration.

Meanwhile, as described above, it is confirmed that in a biological sample obtained from a patient with neurodegenerative diseases, compared to a normal person, the degree of the acetylation of COX2 protein, more specifically the acetylation of S565 residue of COX2 protein, much more specifically the acetylation of S565 residue of COX2 protein represented by SEQ ID NO: 1 is reduced. Therefore, by detecting the degree of the acetylation of the COX2 protein, it is possible to evaluate the diagnosis of neurodegenerative diseases, the progression conditions of the diseases, and the prognosis before and after treatment.

Accordingly, the present invention provides a composition for diagnosing neurodegenerative diseases comprising the antibody or the functional fragment thereof.

In addition, the present invention provides a kit for diagnosing neurodegenerative diseases comprising the antibody or the functional fragment thereof.

The diagnostic kit of the present invention may include not only the antibody or the functional fragment thereof, but also one type or one or more other component compositions, solutions or devices suitable for the assay method.

More specifically, the kit may be a diagnostic kit comprising essential elements required for performing Western blot, immunofluorescence staining, ELISA, and the like. These kits may include an antibody specific for a control protein. In addition, the kit may include a reagent capable of detecting bound antibodies, for example, labeled secondary antibodies, chromophores, enzymes (in the form conjugated the antibody) and substrates thereof or other materials capable of binding to the antibody, and the like. In addition, the kit of the present invention may include a washing solution or an eluent capable of removing substrates to color-react with the enzyme, non-binding proteins, and the like and retaining only the bound protein marker.

In addition, the kit of the present invention may further comprise an antibody and a fragment or an aptamer of the antibody capable of binding to both non-acetylated and acetylated COX2 proteins (i.e., antibody or functional fragment thereof that recognizes an epitope without including an acetylated residue of the COX2 protein). In this case, the kit of the present invention may more accurately diagnose neurodegenerative diseases to confirm a ratio of the level of acetylated COX2 to the total expression level of COX2.

In the present invention, the types of neurodegenerative diseases are not particularly limited, but may be selected from the group consisting of Alzheimer's disease, Parkinson's disease, progressive supranuclear palsy, multiple system atrophy, olivine-pony-cerebellar atrophy (OPCA), Shay-Drager syndrome, striatal-nigular degeneration, Huntington's disease, amyotrophic lateral sclerosis (ALS), essential tremor, cortical-basal nucleus degeneration, diffuse Lewy body disease, Parkinson's-ALS-dementia complex, Nieman-Pick's disease, Pick's disease, cerebral ischemia and cerebral infarction.

The present invention provides a composition for diagnosing inflammatory diseases comprising the antibody or the functional fragment thereof.

The inflammatory diseases may be selected from the group consisting of dermatitis, allergy, atopic dermatitis, asthma, conjunctivitis, rhinitis, otitis media, sore throat, tonsillitis, pneumonia, gastric ulcer, gastritis, Crohn's disease, inflammatory bowel disease, lupus, hepatitis, cystitis, nephritis, sjogren's syndrome, uveitis, ankylosing spondylitis, endometritis, multiple sclerosis, sepsis, septic shock, chronic obstructive pulmonary disease and arthritis.

On the other hand, according to an embodiment of the present invention, it was confirmed that although the expression level of COX2 protein (both acetylated and non-acetylated COX2 proteins) was increased in blood cells and brain tissues obtained from patients with neurodegenerative diseases compared to normal individuals, the S565 acetylation degree of COX2 protein was rather decreased. Therefore, the ratio of the expression level of the S565-acetylated COX2 protein to the expression level of the total COX2 protein was significantly low in an Alzheimer's animal model.

These results suggest that the ratio of the S565-acetylated COX2 protein to total COX2 protein in microglia in brain tissue of the Alzheimer's animal model can be used as a diagnostic marker for neurodegenerative diseases.

The present invention provides uses of the antibody or the functional fragment thereof for preparing a preparation for diagnosing neurodegenerative diseases.

The present invention provides a method for diagnosing neurodegenerative diseases comprising steps of:
   a) obtaining a sample from a subject;
   b) measuring an acetylation level of COX2 protein by adding the antibody or the functional fragment thereof to the sample; and
   c) comparing the acetylation level of the COX2 protein with that of a normal subject, and determining that a subject having a reduced acetylation level of the COX2 protein compared to the normal subject suffers from neurodegenerative diseases.

In an aspect, the present invention provides a method for diagnosing and treating neurodegenerative diseases of a subject (individual) comprising the following steps:
   i) obtaining a sample from a subject;
   ii) measuring an acetylation level of COX2 protein by adding the antibody or the functional fragment thereof to the sample;
   iii) comparing the acetylation level of the COX2 protein with that of a normal subject, and determining that a subject having a reduced acetylation level of the COX2 protein compared to the normal subject suffers from inflammatory diseases; and
   iv) treating the neurodegenerative diseases by administering a therapeutic drug for treating the neurodegenerative diseases to the determined subject or through surgery. Methods including steps i) to iv) are understood based on the method including steps a) to c) described above.

Step iv) is a step of performing the treatment of the diseases by a means such as administration of a therapeutic drug such as donepezil, surgery, or the like, to the subject in which the disease is diagnosed in step iii).

The present invention provides uses of the antibody or the functional fragment thereof for preparing a preparation for diagnosing inflammatory diseases.

The present invention provides a method for diagnosing inflammatory diseases comprising steps of:
   a) obtaining a sample from a subject;
   b) measuring an acetylation level of COX2 protein by adding the antibody or the functional fragment thereof to the sample; and
   c) comparing the acetylation level of the COX2 protein with that of a normal subject, and determining that a subject having a reduced acetylation level of the COX2 protein compared to the normal subject suffers from inflammatory diseases.

In an aspect, the present invention provides a method for diagnosing and treating inflammatory diseases of a subject (individual) comprising the following steps:
   i) obtaining a sample from a subject;
   ii) measuring an acetylation level of COX2 protein by adding the antibody or the functional fragment thereof to the sample;
   iii) comparing the acetylation level of the COX2 protein with that of a normal subject, and determining that a subject having a reduced acetylation level of the COX2 protein compared to the normal subject suffers from inflammatory diseases; and
   iv) treating the inflammatory diseases by administering a therapeutic drug for treating the inflammatory diseases to the determined subject or through surgery.

Methods including steps i) to iv) are understood based on the method including steps a) to c) described above.

Step iv) is a step of performing the treatment of the diseases by a means such as administration of a therapeutic drug such as dexamethasone and betamethasone, surgery, or the like, to the subject in which the disease is diagnosed in step iii).

The term 'treatment' of the present invention comprehensively refers to improving neurodegenerative diseases or inflammatory diseases, or symptoms thereof, and may include treating or substantially preventing these diseases, or improving the conditions thereof and includes alleviating, treating or preventing a symptom or most of symptoms derived from Alzheimer's disease, but is not limited thereto.

The type of 'therapeutic drug' is not particularly limited as long as the therapeutic drug is any type of drug typically used for the treatment of neurodegenerative diseases or inflammatory diseases. The therapeutic drug is administered to a subject in a 'therapeutically effective dose', wherein the therapeutically effective dose for patients may be determined by those skilled in the art by considering various factors, such as age, weight, health condition, and sex of a patient, severity of a disease, diet and excretion rate, etc. as well as unique properties, route of administration, and treatment times of the drug. The route of administration of the therapeutic drug is not particularly limited, and the therapeutic drug may be administered orally or parenterally, and includes both local administration and systemic administration. The parenteral administration is not limited thereto, but may be, for example, intranasal drug application, subcutaneous injection, and the like, and as another example, a method such as intramuscular injection, intravenous injection, or the like may be used.

The 'sample' of the present invention is isolated and obtained from a subject suspected of having diseases, but is not limited thereto, and may be selected from the group consisting of cells, tissues, blood, serum, plasma, saliva, mucosa, and urine. The "subject" may be animals, preferably animals including mammals, particularly humans, and may be cells, tissues, organs, etc. derived from animals. The subject may be a patient requiring the therapeutic effects.

The term "comprising" used herein is used in the same meaning as "including" or "characterized by", and does not exclude additional ingredients or steps of the method which are not specifically mentioned in the composition or the method according to the present invention. The term "consisting of" means excluding additional elements, steps or ingredients, etc., unless otherwise described. The term "essentially consisting of" means including materials or steps which do not substantially affect basic properties thereof in addition to the described materials or steps within the range of the composition or the method.

Advantageous Effects

According to the present invention, the antibody or the functional fragment thereof specifically binds to an acetylated residue of COX2 protein and thus can be very effectively used for diagnosing neurodegenerative diseases, inflammatory diseases, and the like in which the degree of acetylation of S565 residue of the COX2 protein is reduced.

DESCRIPTION OF DRAWINGS

FIG. 7 illustrates a light chain variable region DNA sequence and a peptide amino acid sequence of a monoclonal antibody (9F7-2) that recognizes a peptide (PFTSacFSVPDPELI) of SEQ ID NO: 3 as an epitope.

FIG. 8 illustrates a heavy chain variable region DNA sequence and a peptide amino acid sequence of a monoclonal antibody (9F7-2) that recognizes a peptide (PFTSacFSVPDPELI) of SEQ ID NO: 3 as an epitope.

FIG. 9 illustrates a light chain variable region DNA sequence and a peptide amino acid sequence of a monoclonal antibody (44C7C8) that recognizes a peptide (GCPFTSacFSVPD) of SEQ ID NO: 4 as an epitope.

FIG. 10 illustrates a heavy chain variable region DNA sequence and a peptide amino acid sequence of a monoclonal antibody (44C7C8) that recognizes a peptide (GCPFTSacFSVPD) of SEQ ID NO: 4 as an epitope.

MODES FOR THE INVENTION

Figure 1A:
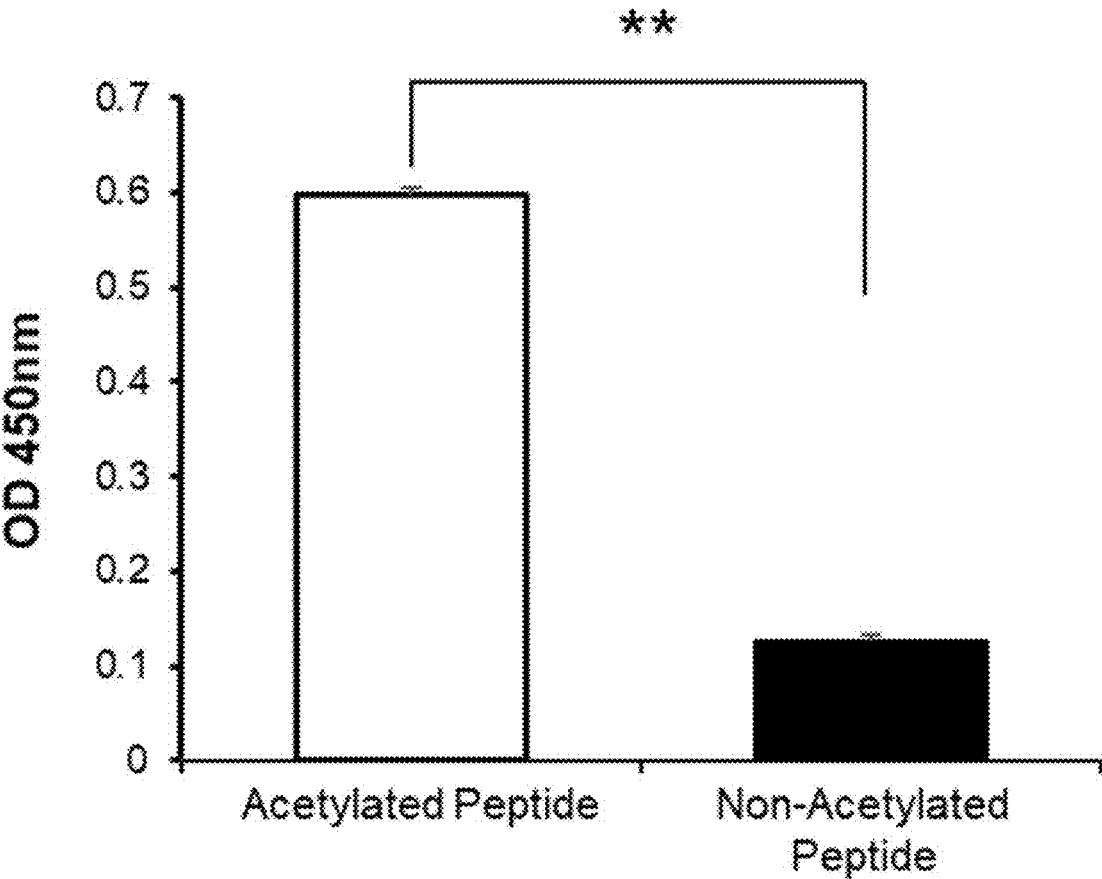
FIGS. 1A and 1B illustrate an absorbance result of analyzing whether to detect separately an acetylated peptide (PFTSacFSVPDPELI (SEQ ID NO: 3)) and a non-acetylated peptide (PFTSFSVPDPELI (SEQ ID NO: 45)) by ELISA assay after preparing a monoclonal antibody (9F7-2) that recognizes a peptide (PFTSacFSVPDPELI) including acetylated S565 residue in COX2 as an epitope (FIG. 1A), and a result of detecting and then quantifying an expression level of COX2 including acetylated S565 residue in wild-type human microglia and S565A-mutated human microglia by ELISA assay (FIG. 1B).

Hereinafter, the present invention will be described in detail by the following Examples. However, the following Examples are just illustrative of the present invention, and the contents of the present invention are not limited to the following Examples.

Experiment Method

1. Preparation of Antibody 1-1: Preparation of Hybridoma Cell for Fabricating S565 Acetylated Monoclonal Antibody of COX2

Peptides of (i) SEQ ID NO: 3 (PFTSacFSVPDPELI) and (ii) SEQ ID NO: 4 (GCPFTSacFSVPD) including S565 residue acetylated in COX-2 protein of SEQ ID NO: 1 were prepared, and then the corresponding peptides were immunized in wild-type BALB/c mice, and monoclonal antibodies thereto were established by a cell fusion method. 5 to $7 \times 10^6$ splenocytes obtained from the immunized mice were fused with SP2/O myeloma cells to prepare a hybridoma cell line.

1-2: Screening Method for Selecting Clones

First, IgG expression was screened twice using a 96-well plate. Then, positive expression clones were transferred to a 24-well plate, and a cell supernatant (=clones) of the growing cells was screened by ELISA using the prepared epitope peptide of SEQ ID NO: 3 or SEQ ID NO: 4.

1-3: Screening Method Using Epitope Peptide

50 μl/well of a hybridoma supernatant (1:500) in a coating buffer was added to a 96-well plate, and then coated at 4° C. for 16 hours. After the plate was washed with PBS/Tween, 300 μl/well of a blocking solution was applied at RT for 1 hour. 50 μl (500 μg/ml) of the peptide of SEQ ID NO: 3 or SEQ ID NO: 4 was incubated at room temperature for 2 hours. After the washing step, a COX2 antibody (abcam, ab15191) attached with biotin using a Biotin conjugation kit (abcam, ab201796) was applied to the plate at a concentration of 0.5 μg/ml at RT for 1 hour. Next, a peroxidase (HRP) solution (1:1000) was applied onto the plate for 1 hour at RT. After the final washing, the detection was performed with TMB (3-3',5,5'-tetramethylbenzidine) (phosphatase substrate for HRP) and the plate was read at 405 nm using an ELISA plate reader. The result was expressed by optical density (O.D.). As a negative control, the non-acetylated peptide of SEQ ID NO: 3 or SEQ ID NO: 4 (500 μg/ml) was used.

1-4: Clone Screening Method Using COX2 S565 Mutant Cells

In order to prepare an antibody specific for the acetylation of S565 residue in COX2 protein, the hybridoma cell supernatant was used to determine whether COX2 S565 was acetylated in normal microglia and microglia induced by mutation at S565 residue of the COX2 protein. S565 mutant microglia were formed by transfecting a protein (S565A) substituting Serine 565 of COX2 with Alanine into normal microglia (Applied Biologics Materials, TO251). The normal microglia and the S565 mutant microglia were lysed by adding an RIPA solution (Cell signaling, 9806S), and then the cell lysate was centrifuged (13,000×g, 10 minutes) to obtain a supernatant, and then the amount of protein was quantified and ELISA screening was performed using 100 μg/ml of protein.

A standard curve was obtained by step-diluting the peptide (500 μg/ml) of SEQ ID NO: 3 or SEQ ID NO: 4, and the value of COX2 protein acetylated in S565 was calculated by substituting an optical density (O.D.) value obtained from the sample into the obtained standard curve.

1-5: Clone Screening

Monoclonal antibodies (hereinafter, referred to as 9F7-2 and 9F7-2) that were positive for the peptide of SEQ ID NO: 3 or SEQ ID NO: 4 and detected the COX2 protein with acetylated S565 in normal microglia compared to microglia inducing S565 mutation (S565A) were screened and finally, 9F7-2 and 44C7F5 hybridoma cells of single colonies were secured by a limiting dilution method.

1-6: Amino Acid Sequencing of Prepared Antibody

Total RNA was isolated from the selected hybridoma cells according to a technical manual of a TRIzol® reagent (Ambion, 15596-026). Then, total RNA was reverse-transcribed into cDNA using isotype-specific anti-sense primers or universal primers according to a technical manual of a PrimeScript TM 1st Strand cDNA Synthesis kit (Takara, 6110A). Antibody fragments of heavy and light chains were amplified according to a standard operating procedure (SOP) for rapid amplification. The amplified antibody fragments were individually cloned with a standard cloning vector. Colony PCR was performed to screen clones with inserts of a correct size.

2. Mouse

A mouse experiment has been approved by the Kyungpook National University Institutional Animal Care and Use Committee (IACUC). A transgenic mouse line overexpressing APPswe (hAPP695swe) or PS1 (presenilin-1M146V) based on C57BL/6 mice (Charles River, UK) was used [Hereinafter, APP mouse: mouse overexpressing APPswe, PS1 mouse: mouse overexpressing presenilin-1M146V; GlaxoSmithKline].

3. ELISA Assay

Samples such as acetylated peptides of SEQ ID NO: 3 and SEQ ID NO: 4, a non-acetylated peptide having the same amino acid sequence as the peptides of SEQ ID NO: 3 and SEQ ID NO: 4, but non-acetylated serine, peripheral blood mononuclear cells (PBMCs) of mouse and human, and the like were prepared.

The sample preparation was performed according to the following procedure. After collecting mouse and human blood, the blood was transferred to a heparin tube and reacted for 30 minutes. The reacted blood was placed on the same amount of Histopaque (sigma, 10771) and centrifuged (400 g, 30 minutes). After centrifugation, a middle PBMC layer was separated and washed. After washing, the PBMCs were lysed by adding an RIPA solution (Cell signaling, 9806S), and then the cell lysate was centrifuged (13,000×g, 10 minutes) to obtain a supernatant, and then the amount of protein was quantified and ELISA assay was performed using 100 μg/ml of protein.

50 μl/well of the monoclonal antibodies 9F7-2 and 44C7F5 (0.1 μg/ml) prepared in Experiment 1 in the coating buffer were added to each well of a 96-well plate, and coated at 4° C. for 16 hours. After the plate was washed with PBS/Tween, 300 μl/well of a blocking solution was applied at RT for 1 hour. 50 μl of a PBMC sample (100 μg/ml) was treated and incubated at RT for 2 hours. After the washing step, a COX2 antibody (abcam, ab 15191) attached with biotin using a Biotin conjugation kit (abcam, ab201796) was applied onto the plate at a concentration of 0.5 μg/ml at RT for 1 hour. Next, a peroxidase (HRP) solution (1:1000) was applied onto the plate for 1 hour at RT. After the final washing, the detection was performed with TMB (3-3',5,5'-tetramethylbenzidine) (phosphatase substrate for HRP) and the plate was read at 405 nm using an ELISA plate reader. A standard curve was obtained by step-diluting the peptide (500 μg/ml) of SEQ ID NO: 3 or SEQ ID NO: 4, and the amount of COX2 protein acetylated in S565 residue was calculated by substituting an optical density (O.D.) value obtained from the sample to the Standard curve.

4. Immunofluorescence Assay

In cerebral tissues of wild type (WT) and APP/PS1 9-month-old mice and human (normal group and Alzheimer's patient group) cerebral tissues, the expression level of COX2 protein with acetylated S565 residue was confirmed by immunofluorescence using each monoclonal antibody (9F7-2 or 44C75F) prepared in Experimental Method 1 above.

The cerebra of 9-month-old normal control and APP/PS1 mice were extracted and then fixed with 4% paraformaldehyde. The extracted cerebral tissue was sectioned using a floating section. For human (normal group and Alzheimer's patient group) cerebral tissues, Paraffin sections provided by each of 6 persons from the Netherlands brain bank were used.

The mouse and human (normal group and Alzheimer's patient group) cerebral tissue sections were treated with each (release 9.1; SAS Institute Inc., Cary, NC). * p<0.05, ** p<0.01 were considered significant.

Experimental Result

1. Preparation of Antibody 9F7-2 Using Region (PFT-SacFSVPDPELIC) Including Acetylated S565 Residue in COX2 as Epitope A monoclonal antibody 9F7-2, that recognized 13 amino acids of PFTSacFSVPDPELI including acetylated S565 in COX2, was prepared according to the experimental method. An amino acid sequence of the prepared monoclonal antibody 9F7-2 and a polynucleotide sequence encoding the amino acid sequence were analyzed, and the sequencing results were shown in Table 1 below.

| | | Amino acid sequence | DNA sequence |
|---|---|---|---|
| Light chain variable region (VL) | CDR-L1 | RSSQSIVHRNGFTYLE (SEQ ID NO: 5) | AGATCTAGTCAGAGCATTGTACATCGTAATGGA TTCACCTACTTAGAA (SEQ ID NO: 13) |
| | CDR-L2 | QVSNRFS (SEQ ID NO: 6) | CAAGTTTCCAACCGATTTTCT (SEQ ID NO: 14) |
| | CDR-L3 | FQGSHVPPT (SEQ ID NO: 7) | TTTCAGGGTTCACATGTTCCTCCGACA (SEQ ID NO: 15) |
| | Full (FR1-CDR1-FR2-CDR2-FR3-CDR3-FR4) DVLMTQTPLSLPVSLGDQASISCRSSQSIVHRNGFTYLEWYLQKPGQSPKLLIYQVSNRFSGVPDR FSGSGSGTDFTLKISRVEAEDLGVYYCFQGSHVPPTFGGGTKLEIK (SEQ ID NO: 11) GATGTTTTGATGACCCAAACTCCACTCTCCCTGCCTGTCAGTCTTGGAGATCAAGCCTCCATCT CTTGCAGATCTAGTCAGAGCATTGTACATCGTAATGGATTCACCTACTTAGAATGGTACCTGCA GAAACCAGGCCAGTCTCCAAAGCTCCTGATCTACCAAGTTTCCAACCGATTTTCTGGGGTCCC AGACAGGTTCAGTGGCAGTGGATCAGGGACAGATTTCACACTCAAGATCAGCAGAGTGGAGG CTGAGGATCTGGGAGTTTATTACTGCTTTCAGGGTTCACATGTTCCTCCGACATTCGGTGGAGG CACCAAGCTGGAAATCAAA (SEQ ID NO: 19) | | |
| Heavy chain variable region (VH) | CDR-H1 | DYLLG (SEQ ID NO: 8) | GACTACTTACTAGGT (SEQ ID NO: 16) |
| | CDR-H2 | DIYPGGTYIKYNEKFKG (SEQ ID NO: 9) | GATATTTACCCTGGAGGTACTTATATTAAGTACA ATGAGAAGTTCAAGGGC (SEQ ID NO: 17) |
| | CDR-H3 | GRNDEKGDY (SEQ ID NO: 10) | GGGAGGAACGACGAGAAGGGGGACTAC (SEQ ID NO: 18) |
| | Full (FR1-CDR1-FR2-CDR2-FR3-CDR3-FR4) QVQLQQSGAELVRPGTSVKISCKASGYTFTDYLLGWVKQRPGHGLEWIGDIYPGGTYIKYNEKF KGKATLTADTSSSTAYMQLSSLTSEDSAVYFCARGRNDEKGDYWGQGTSVTVSS (SEQ ID NO: 12) CAGGTCCAGCTGCAGCAGTCTGGAGCTGAGCTGGTAAGACCTGGGACTTCAGTGAAGATATC CTGCAAGGCTTCTGGCTACACCTTCACTGACTACTTACTAGGTTGGGTAAAGCAGAGGCCTGG ACATGGACTTGAGTGGATTGGAGATATTTACCCTGGAGGTACTTATATTAAGTACAATGAGAAG TTCAAGGGCAAGGCCACACTGACTGCAGACACATCCTCCAGCACTGCCTACATGCAACTCAG TAGCCTGACATCTGAGGACTCTGCTGTCTACTTCTGTGCAAGAGGGAGGAACGACGAGAAGG GGGACTACTGGGGTCAAGGAACCTCAGTCACCGTCTCCTCA (SEQ ID NO: 20) | | |

45 monoclonal antibody (9F7-2 or 44C75F) (mouse, 1:100) prepared in Experimental Method 1, an anti-COX2 antibody (goat, 1:500, Abcam) and an anti-Iba1 antibody (rabbit, 1:500, Wako) and cultured at 4° C. for 16 hours. Thereafter, in the presence of AlexaFluor conjugates rabbit 488, goat 594, and mouse 674 antibodies (1:500; Life Technologies, Waltham, MA, USA), secondary antibodies were incubated for 2 hours and subjected to glass coverslipping. In the cerebral tissues, a ratio of cells stained with 9F7-2 and 44C75F antibodies among cells stained with anti-COX2 and anti-Iba1 was quantified and analyzed using MetaMorph (Molecular Devices, USA).

5. Statistical Analysis

A T-test for students was performed to compare two groups, while for comparison of multiple groups, repeated measurement analysis of a Tukey's HSD test and a variance test was performed according to an SAS statistical package To determine whether the prepared monoclonal antibody 9F7-2 may separately target the acetylated peptide (PFT-SacFSVPDPELI (SEQ ID NO: 3)) and the non-acetylated control peptide (PFTSFSVPDPELI (SEQ ID NO: 45)), ELISA assay was performed in a 96-well plate coated with the antibody 9F7-2.

As a result, as illustrated in FIG. 1A, it was confirmed that the acetylated peptide (PFTSacFSVPDPELI (SEQ ID NO: 3)) exhibited higher absorbance than that of the non-acetylated control peptide (PFTSFSVPDPELI (SEQ ID NO: 45)).

In addition, in order to confirm whether the prepared antibody may specifically target the S565 acetylated COX2 protein even in human-derived microglia, the present inventors treated an extract from a control cell (control) and a cell inducing a mutant (S565A) substituting S565 residue of COX2 with alanine with the antibody 9F7-2.

Figure 1B:
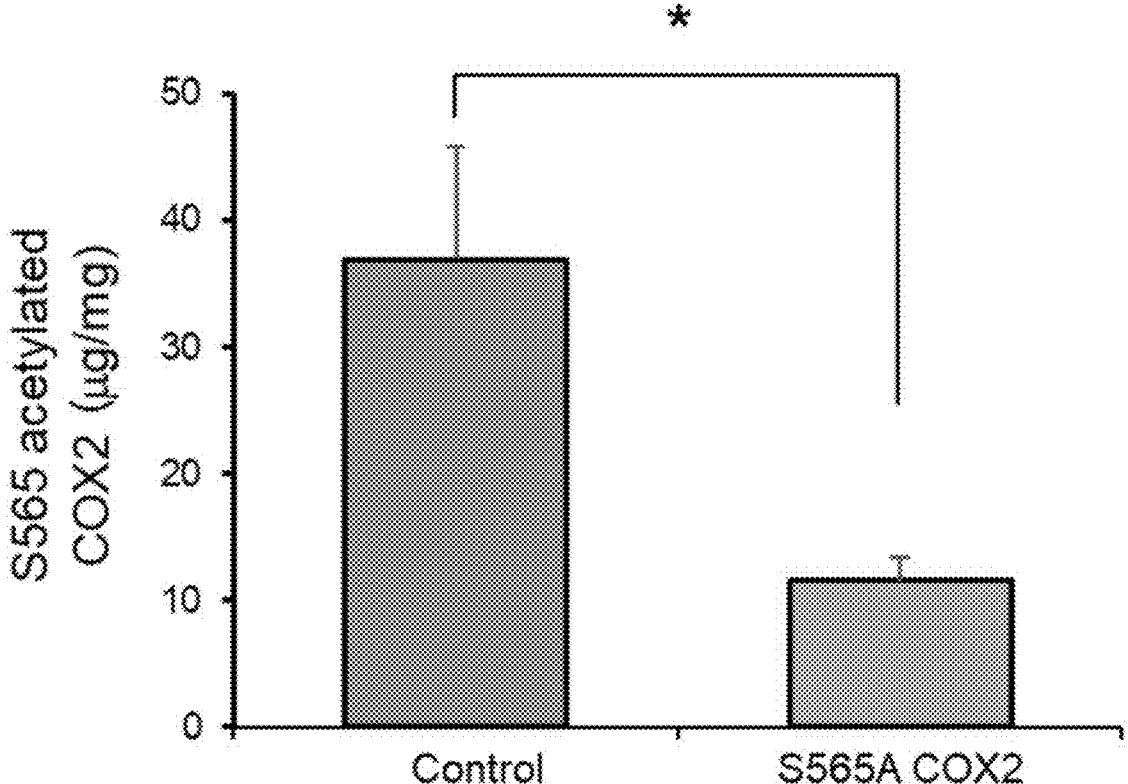

As a result, as illustrated in FIG. 1B, it was confirmed that the detection amount of acetylated COX2 protein was decreased in microglia (S565A COX2) mutated in S565 compared to normal human-derived microglia (control).

Based on these results, it was confirmed that the prepared monoclonal antibody 9F7-2 specifically targeted the acetylated S565 residue in the COX2 protein, and the epitope of the antibody was a sequence of PFTSacFSVPDPELI (SEQ ID NO: 3) including the acetylated S565 residue in the COX2 protein.

2. Confirmation of Reduction of S565 Acetylation of COX2 in Blood Cells and Brain Tissue of Alzheimer's Animal Model Using Antibody 9F7-2

The present inventors confirmed the degree of S565 acetylation of COX2 protein in blood cells (PBMC) obtained from an Alzheimer's animal model using the prepared monoclonal antibody 9F7-2.

Figure 2A:
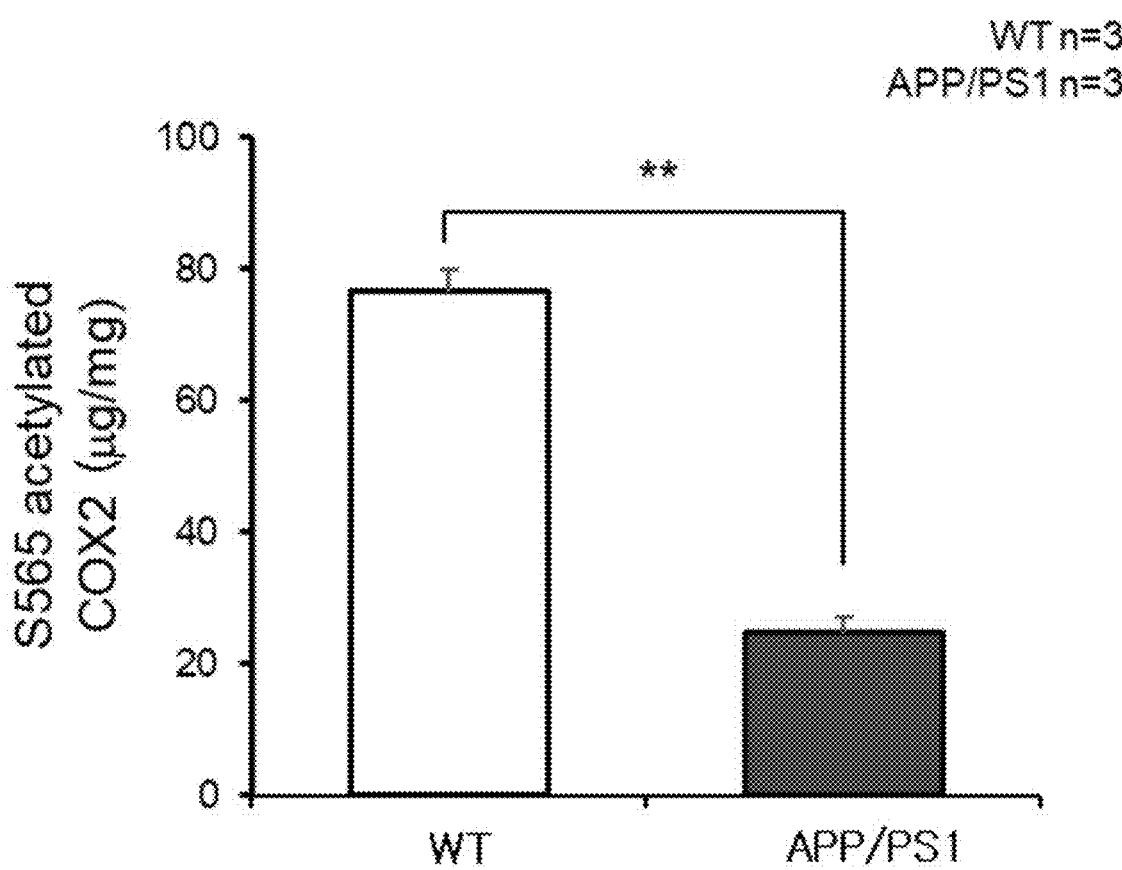
FIGS. 2A and 2B illustrate a result of confirming and quantifying an expression level of COX2 including acetylated S565 residue by ELISA assay using a monoclonal antibody (9F7-2) according to the present invention after extracting a protein in peripheral blood mononuclear cells (PBMCs) obtained from a normal mouse (WT) and an Alzheimer's animal model (APP/PS1) (FIG. 2A), and a graph showing a ratio of COX2 including acetylated S565 residue to total COX2 protein by observing total COX2 protein (COX2, red) and COX2 including acetylated S565 residue (9F7-2, blue) by immunofluorescence staining in microglia (Iba1, microglia marker, green) in brain tissue of a normal mouse (WT) and an Alzheimer's animal model (APP/PS1) and quantifying the total COX2 protein and the COX2 (FIG. 2B).

As a result, as illustrated in FIG. 2A, as compared with a wild-type mouse (WT), it was confirmed that the degree of S565 acetylation of COX2 protein detected by the monoclonal antibody 9F7-2 was reduced in blood cells (PBMC) of an Alzheimer's animal (APP/PS1).

In addition, the present inventors reconfirmed the expression level of COX2 protein with acetylated S565 residue in microglia in the brain tissue of a wild-type animal (WT) and an Alzheimer's animal model (APP/PS1) using the monoclonal antibody 9F7-2.

Figure 2B:
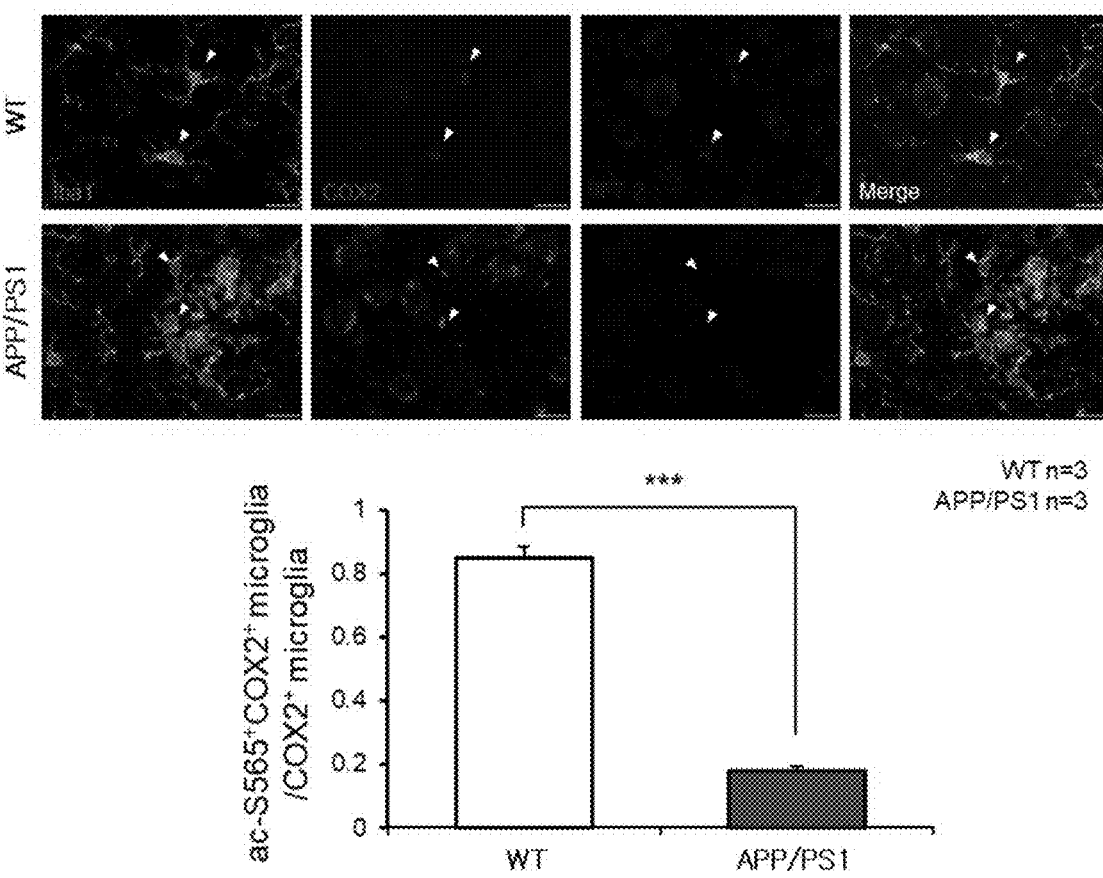

As a result, as illustrated in FIG. 2B, as compared with a wild-type animal (WT), it was confirmed that the degree of S565 acetylation of COX2 protein detected by the monoclonal antibody 9F7-2 was reduced in microglia of an Alzheimer's animal (APP/PS1). In particular, although the expression level of COX2 protein (both COX2 proteins with or without acetylated S565) increased in microglia of the Alzheimer's animal compared to the wild-type animal, it was confirmed that the degree of S565 acetylation of COX2 protein was rather decreased. Therefore, a ratio of the expression level of the S565 acetylated COX2 protein to the expression level of the total COX2 protein (ac-S565+ COX2+microglia/COX2+microglia) was significantly low in the Alzheimer's animal model (bottom graph of FIG. 2B).

Through the results, it was confirmed that the degree of S565 acetylation of the COX2 protein detected by the monoclonal antibody 9F7-2 in blood cells and microglia of the Alzheimer's animal model was significantly reduced, which coincided with the result of a previous study (Korean Patent Application No. 10-2018-0127656).

Furthermore, through the results of the example, it was confirmed that the ratio of the S565 acetylated COX2 protein to the total COX2 protein in the microglia of the brain tissue of the Alzheimer's animal model was significantly low as compared with a normal animal, and these results suggested the applicability of the ratio of the S565 acetylated COX2 protein to the total COX2 protein as a diagnostic marker for neurodegenerative diseases.

3. Confirmation of Reduction of S565 Acetylation of COX2 Detected by Antibody 9F7-2 in Blood Cells and Brain Tissue of Alzheimer's Patient The present inventors confirmed the degree of S565 acetylation of COX2 protein in blood cells (PBMC) obtained from an Alzheimer's patient using the prepared monoclonal antibody 9F7-2.

Figure 3A:
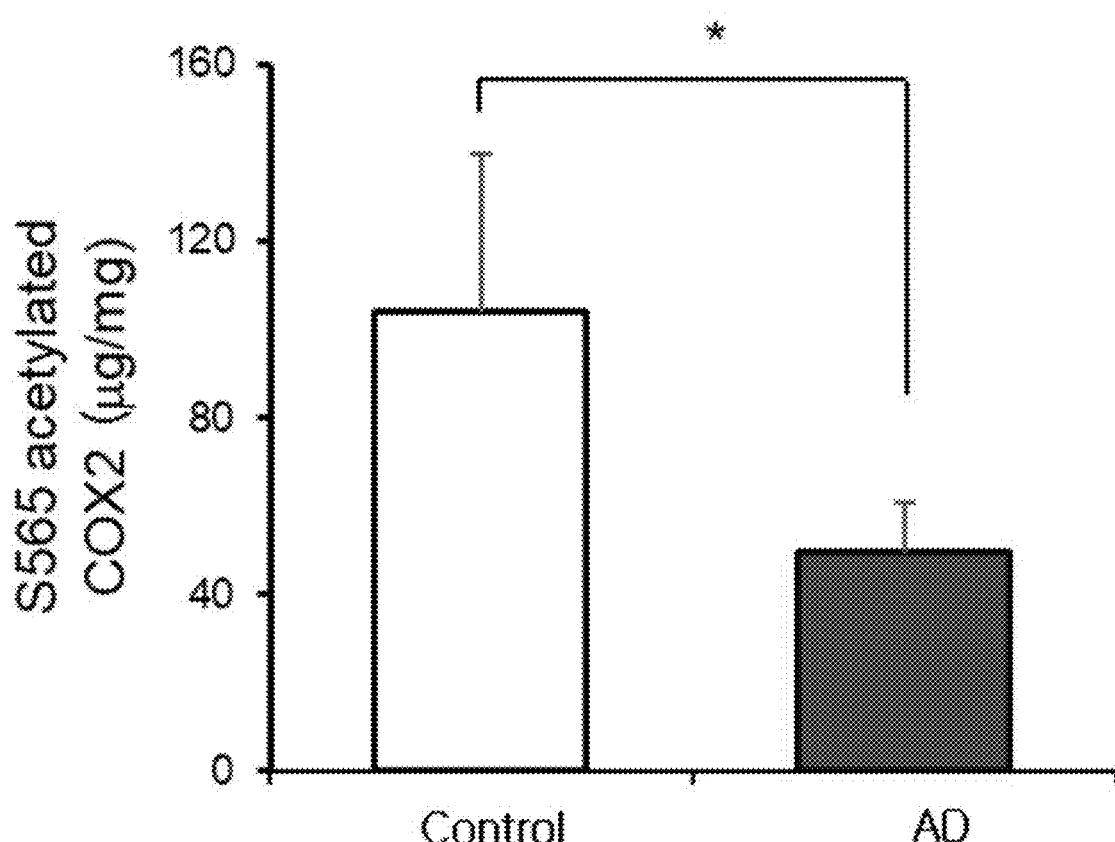
FIGS. 3A and 3B illustrate a result of confirming an expression level of COX2 including acetylated S565 residue by ELISA assay using a monoclonal antibody (9F7-2) according to the present invention after extracting a protein in peripheral blood mononuclear cells (PBMCs) obtained from a normal person (Control) and an Alzheimer's patient (AD) (FIG. 3A), and a graph showing a ratio of COX2 including acetylated S565 residue to total COX2 protein by observing total COX2 protein (COX2, red) and COX2 including acetylated S565 residue (9F7-2, blue) by immunofluorescence staining in microglia (Iba1, microglia marker, green) in brain tissue of a normal person (Control) and an Alzheimer's patient (AD) and quantifying the total COX2 protein and the COX2 (FIG. 3B).

As a result, as illustrated in FIG. 3A, as compared with a control, it was confirmed that the degree of S565 acetylation of COX2 protein detected by the monoclonal antibody 9F7-2 was reduced in blood cells (PBMC) of the Alzheimer's patient.

In addition, the present inventors reconfirmed the expression level of COX2 protein with acetylated S565 residue in microglia in the brain tissue of the control and the Alzheimer's patient using the monoclonal antibody 9F7-2.

Figure 3B:
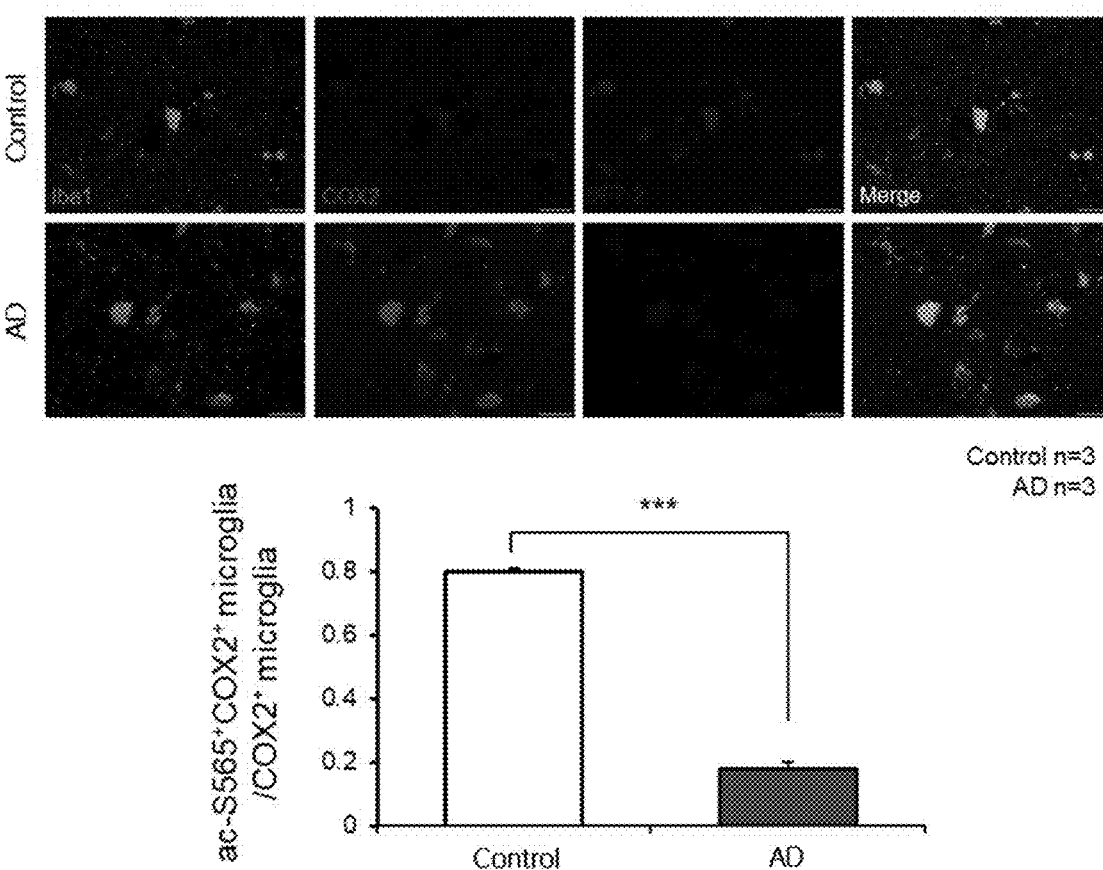

As a result, as illustrated in FIG. 3B, as compared with a control, it was confirmed that the degree of COX2 S565 acetylation detected by the monoclonal antibody 9F7-2 was reduced in microglia of the Alzheimer's patient. In particular, although the expression level of COX2 protein (both COX2 proteins with or without acetylated S565) increased in microglia of the Alzheimer's patient compared to the control, it was confirmed that the degree of S565 acetylation of COX2 protein was rather decreased. Therefore, a ratio of the expression level of the S565 acetylated COX2 protein to the expression level of the total COX2 protein (ac-S565+ COX2+microglia/COX2+microglia) was significantly low in the Alzheimer's patient (bottom graph of FIG. 3B).

Through the results, it was confirmed that the degree of S565 acetylation of COX2 protein detected by the monoclonal antibody 9F7-2 in blood cells and microglia of the Alzheimer's patient was significantly reduced, and it was confirmed that the ratio of the S565 acetylated COX2 protein to the total COX2 protein in the microglia of the brain tissue of the Alzheimer's patient was significantly low as compared with the control. The result coincided with the Alzheimer's animal result of FIG. 2 and suggested the applicability of the ratio of the S565 acetylated COX2 protein to the total COX2 protein as a diagnostic marker for neurodegenerative diseases.

4. Preparation of Antibody 44C7C8 Using Region (GCPFT-SacFSVPD) Including Acetylated S565 Residue in COX2 as Epitope The present inventors prepared a monoclonal antibody 44C7C8 having GCPFTSacFSVPD (SEQ ID NO: 4) as an epitope, which consisted of 11 amino acids shorter than 14 amino acids of PFTSacFSVPDPELIC (SEQ ID NO: 3) sequence including acetylated S565 in COX2 illustrated in FIG. 1. An amino acid sequence of the prepared monoclonal antibody 44C7C8 and a polynucleotide sequence encoding the amino acid sequence were analyzed, and the sequencing results were shown in Table 2 below.

TABLE 2

| | | Amino acid sequence | DNA sequence |
|---|---|---|---|
| Light chain variable region (VL) | CDR-L1 | KSSQSLLYSRNQKNYLA (SEQ ID NO: 21) | AAGTCCAGTCAGAGCCTTTTATATAGTAGAA ATCAAAAGAACTACTTGGCC (SEQ ID NO: 29) |
| | CDR-L2 | WASTRES (SEQ ID NO: 22) | TGGGCATCCACTAGGGAATCT (SEQ ID NO: 30) |
| | CDR-L3 | QQYYTYPFT (SEQ ID NO: 23) | CAGCAATATTATACCTATCCATTCACG (SEQ ID NO: 31) |
| | Full (FR1-CDR1-FR2-CDR2-FR3-CDR3-FR4) DIVMSQSPSSLAVSVEEKVNMSCKSSQSLLYSRNQKNYLAWYQQKPGQSPKLLIYWASTRES GVPDRFTGSGAGTDFTLTISSVKAEDLAVYYCQQYYTYPFTFGSGTKLEIK (SEQ ID NO: 27) GACATTGTGATGTCACAGTCTCCATCCTCCCTAGCTGTGTCAGTTGAAGAGAAGGTTAATA TGAGCTGCAAGTCCAGTCAGAGCCTTTTATATAGTAGAAATCAAAAGAACTACTTGGCCT GGTACCAGCAGAAACCAGGGCAGTCTCCTAAACTACTGATTTACTGGGCATCCACTAGGG AATCTGGGGTCCCTGATCGCTTCACAGGCAGTGGAGCTGGGACAGATTTCACTCTCACCA | | |

TABLE 2-continued

| | Amino acid sequence | DNA sequence |
|---|---|---|
| | TCAGCAGTGTGAAGGCTGAAGACCTGGCAGTTTATTACTGTCAGCAATATTATACCTATCC ATTCACGTTCGGCTCGGGGACAAAGTTGGAAATAAAA (SEQ ID NO: 35) | |
| Heavy chain variable region (VH) | CDR-H1 SGYYWN (SEQ ID NO: 24) CDR-H2 YISYDGSNNYNPSLKN (SEQ ID NO: 25) CDR-H3 GADYYGNTYFYFDV (SEQ ID NO: 26) Full (FR1-CDR1-FR2-CDR2-FR3-CDR3-FR4) DVQLQESGPGLVKPSQSLSLTCSVTGYSITSGYYWNWIRQFPGNKLEWMGYISYDGSNNYNP SLKNRISITRDTYKKQFFLKLNSVTTEDTATYYCARGADYYGNTYFYFDVWGAGTTVTVSS (SEQ ID NO: 28) GATGTACAGCTTCAGGAGTCAGGACCTGGCCTCGTGAAACCTTCTCAGTCTCTGTCTCTC ACCTGCTCTGTCACTGGCTACTCCATCACCAGTGGTTATTACTGGAACTGGATCCGGCAGT TTCCAGGAAACAAACTGGAATGGATGGGCTACATAAGCTACGACGGTAGCAATAACTACA ACCCATCTCTCAAAAATCGAATCTCCATCACTCGTGACACATATAAGAAGCAGTTTTTCCT GAAGTTGAATTCTGTGACTACTGAGGACACAGCCACATATTACTGTGCAAGGGGGGCTGA TTACTACGGTAATACCTACTTCTACTTCGATGTCTGGGGCGCAGGGACCACGGTCACCGTC TCCTCA (SEQ ID NO: 36) | GACTACTTACTAGGT (SEQ ID NO: 32) GATATTTACCCTGGAGGTACTTATATTAAGTA CAATGAGAAGTTCAAGGGC (SEQ ID NO: 33) GGGAGGAACGACGAGAAGGGGGACTAC (SEQ ID NO: 34) |

Figure 4A:
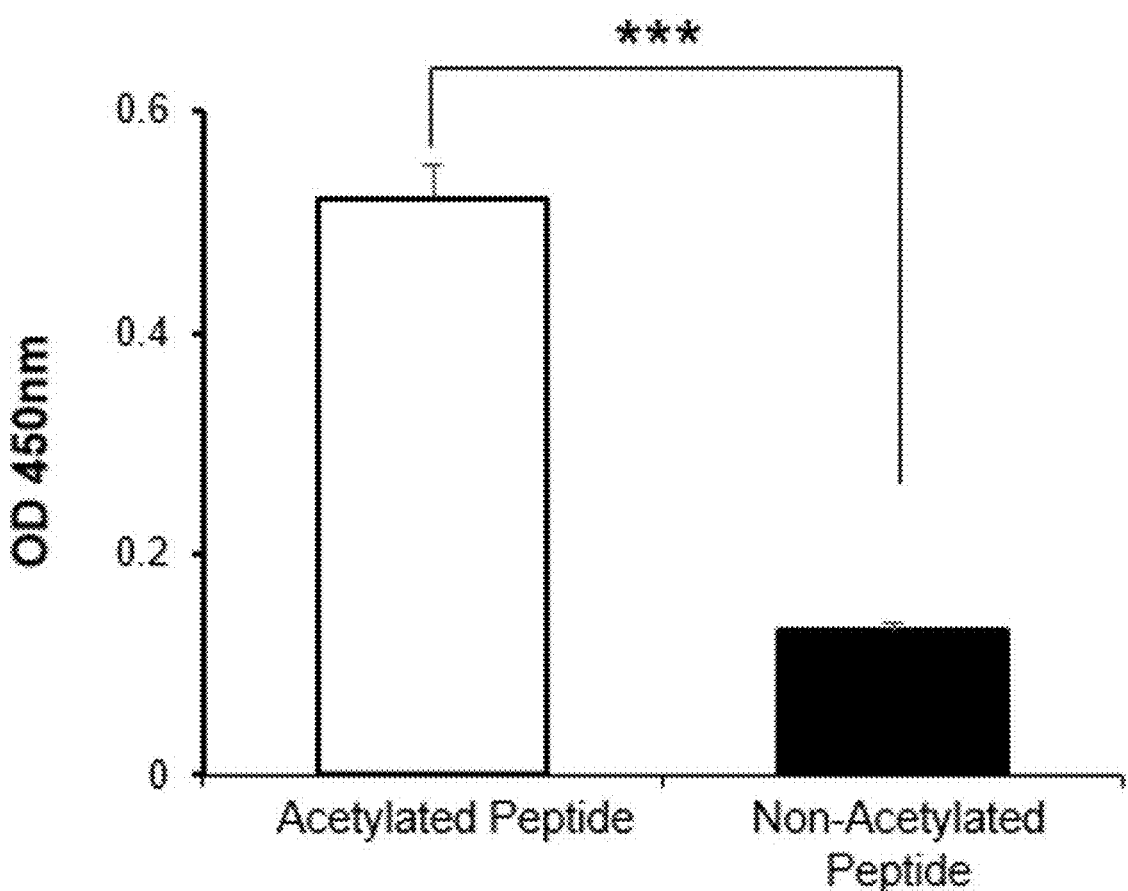
FIGS. 4A and 4B illustrate an absorbance result of analyzing whether to detect separately an acetylated peptide (GCPFTSacFSVPD (SEQ ID NO: 4)) and a non-acetylated peptide (GCPFTSacFSVPD (SEQ ID NO: 46)) by ELISA assay after preparing a monoclonal antibody (44C7C8) that recognizes a peptide (GCPFTSacFSVPD) including S565 residue acetylated in COX2 as an epitope (FIG. 4A), and a result of detecting and then quantifying an expression level of COX2 including acetylated S565 residue in wild-type human microglia and S565A-mutated human microglia by ELISA assay (FIG. 4B).

The prepared monoclonal antibody 44C7C8 exhibited higher absorbance in the acetylated peptide of GCPFT-SacFSVPD (SEQ ID NO: 4) compared to a non-acetylated control peptide used as an epitope sequence (FIG. 4A).

Figure 4B:
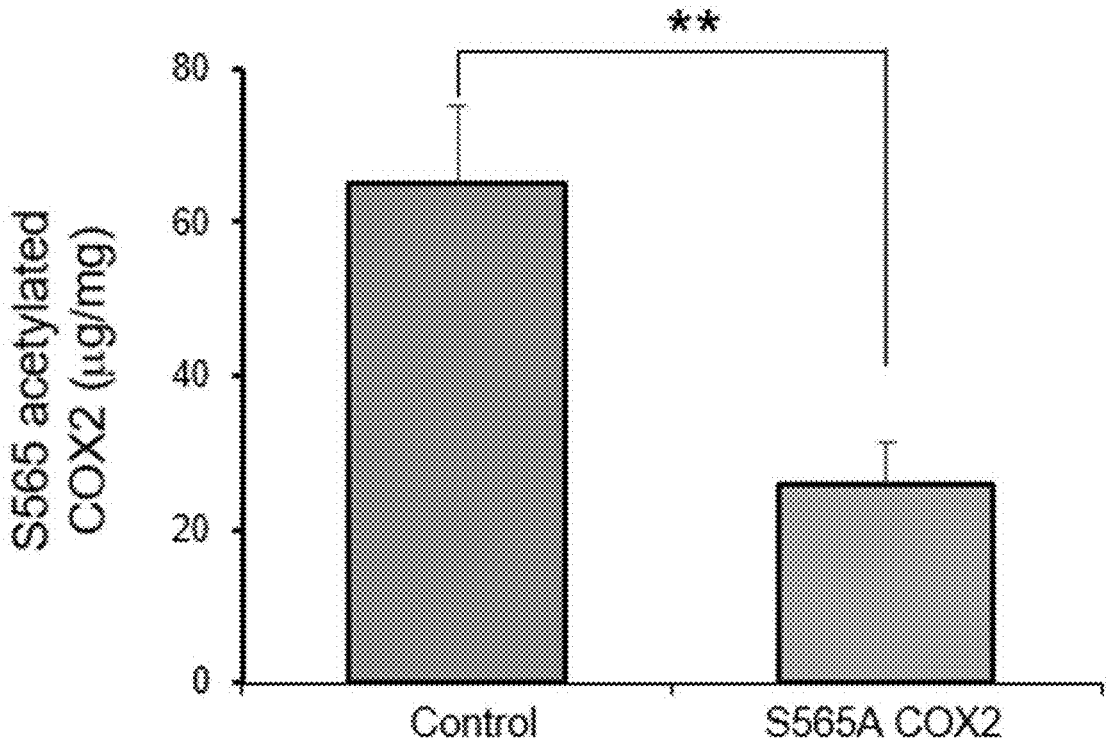

In addition, the present inventors induced a mutation to replace serine 565 residue of COX2 with alanine in human-derived microglia, and confirmed whether the prepared monoclonal antibody 44C7C8 specifically detected acety-lated S565 in COX2. As a result, as illustrated in FIG. 4B, it was confirmed that the absorbance detected by the mono-clonal antibody 44C7C8 prepared in S565-mutated micro-glia (S565A) was reduced compared to normal human-derived microglia. These results indicated that the prepared monoclonal antibody 44C7C8 specifically detected a region of GCPFTSacFSVPD including S565 residue acetylated in COX2. It was confirmed that the prepared monoclonal antibody 44C7C8 specifically detected S565 residue acety-lated in COX2 using an epitope consisting of a shorter amino acid sequence than the monoclonal antibody 9F7-2 prepared in FIG. 1.

Figure 5A:
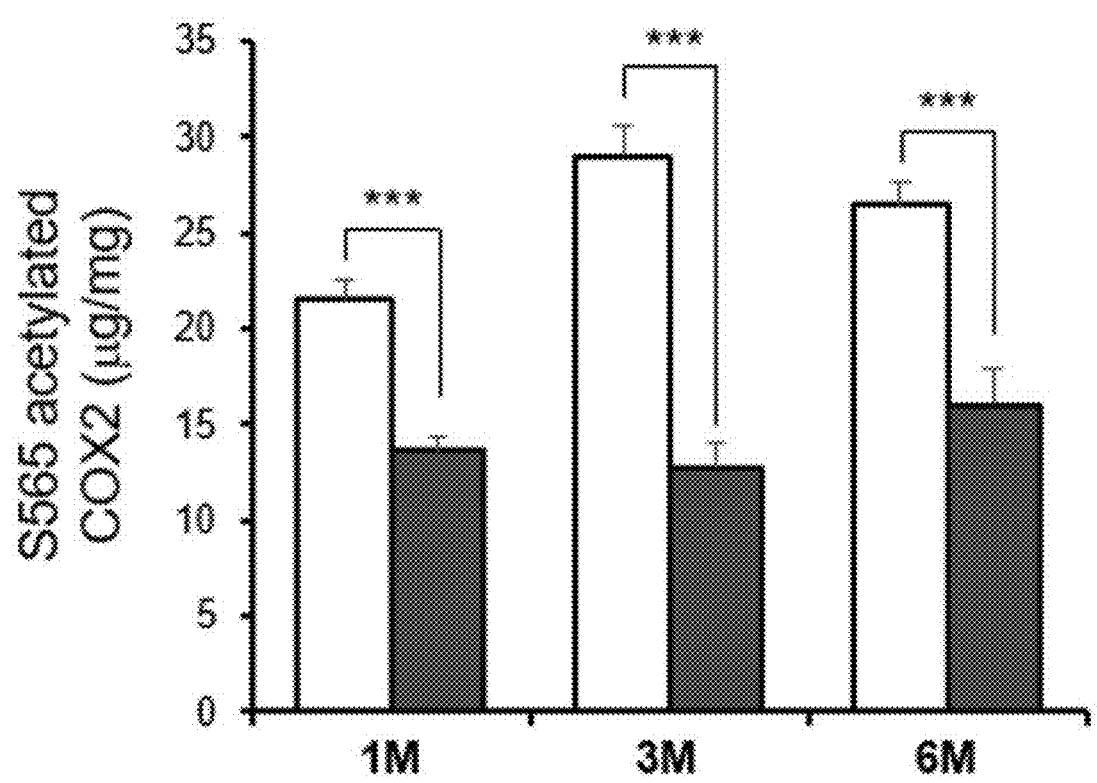
FIGS. 5A and 5B illustrate a result of confirming and quantifying an expression level of COX2 including acetylated S565 residue by ELISA assay using a monoclonal antibody (44C7C8) according to the present invention after extracting a protein in peripheral blood mononuclear cells (PBMCs) obtained from a normal mouse (WT) and an Alzheimer's animal model (APP/PS1) (FIG. 5A), and a graph showing a ratio of COX2 including acetylated S565 residue to total COX2 protein by observing total COX2 protein (COX2, red) and COX2 including acetylated S565 residue (44C7C8, blue) by immunofluorescence staining in microglia (Iba1, microglia marker, green) in brain tissue of a normal mouse (WT) and an Alzheimer's animal model (APP/PS1) and quantifying the total COX2 protein and the COX2 (FIG. 5B).

5. Confirmation of Reduction of S565 Acetylation of COX2 Detected by Antibody 44C7C8 in Blood Cells and Brain Tissue of Alzheimer's Animal Model The present inventors confirmed the degree of COX2 S565 acetylation in blood cells of an Alzheimer's animal model using the prepared monoclonal antibody 44C7C8. As a result, it was confirmed that the COX2 S565 acetylation detected by the prepared monoclonal antibody 44C7C8 in the blood cells of 1, 3, and 6-month-old Alzheimer's animals was reduced compared to a control (FIG. 5A).

Figure 5B:
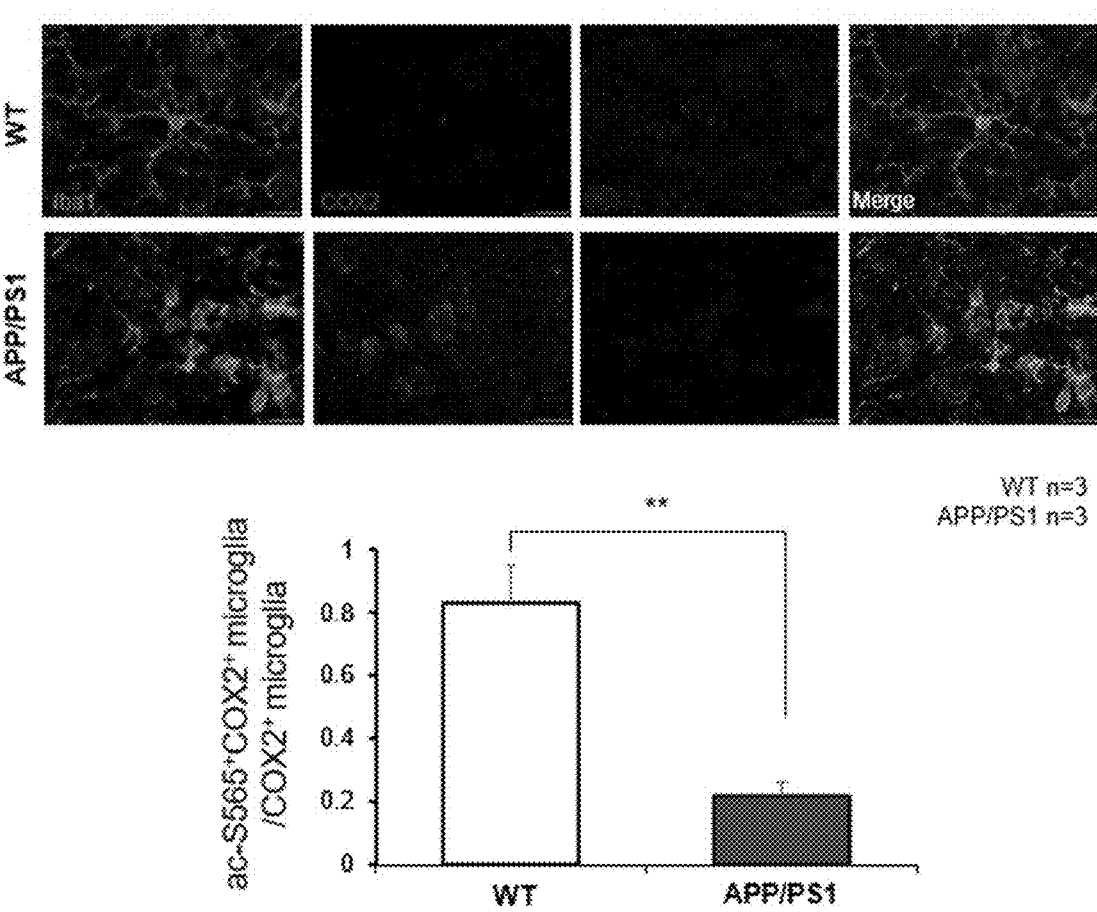

The present inventors reconfirmed the degree of COX2 S565 acetylation in microglia of the brain tissue of an Alzheimer's animal model using the prepared monoclonal antibody 44C7C8. As a result, it was confirmed that the COX2 S565 acetylation detected by the prepared monoclo-nal antibody 44C7C8 was reduced in the microglia of Alzheimer's animals compared to the control, like the blood cell results of FIG. 5A (FIG. 5B).

Therefore, these results confirmed that S565 acetylation was reduced in a region of GCPFTSacFSVPD (SEQ ID NO: 4) of COX2, which was detected by the prepared monoclo-nal antibody 44C7C8 in blood cells and microglia of the Alzheimer's animal model.

Figure 6A:
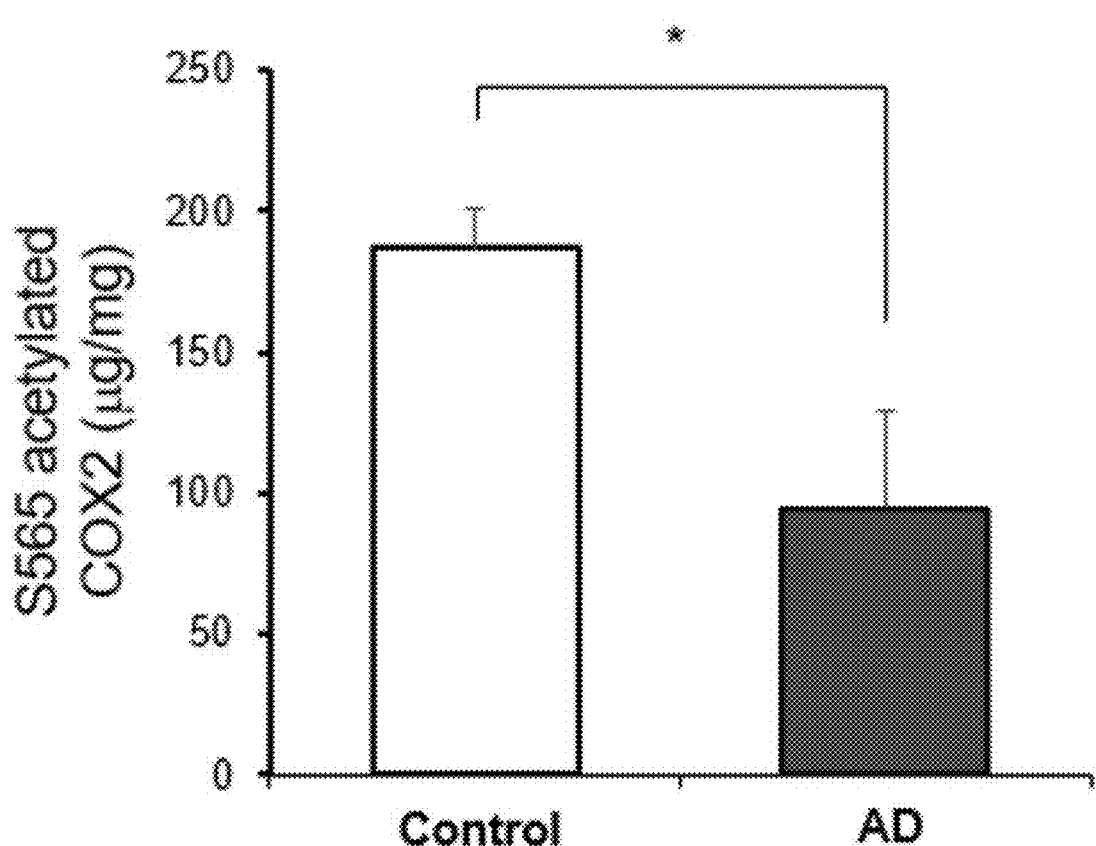
FIGS. 6A and 6B illustrate a result of confirming an expression level of COX2 including acetylated S565 residue by ELISA assay using a monoclonal antibody (44C7C8) according to the present invention after extracting a protein in peripheral blood mononuclear cells (PBMCs) obtained from a normal person (Control) and an Alzheimer's patient (AD) (FIG. 6A), and a graph showing a ratio of COX2 including acetylated S565 residue to total COX2 protein by observing total COX2 protein (COX2, red) and COX2 including acetylated S565 residue (44C7C8, blue) by immunofluorescence staining in microglia (Iba1, microglia marker, green) in brain tissue of a normal person (Control) and an Alzheimer's patient (AD) and quantifying the total COX2 protein and the COX2 (FIG. 6B).

6. Confirmation of Reduction of S565 Acetylation of COX2 Detected by Antibody 44C7C8 in Blood Cells and Brain Tissue of Alzheimer's Patient The present inventors confirmed the degree of COX2 S565 acetylation in blood cells of an Alzheimer's patient using the prepared monoclonal antibody 44C7C8. As a result, it was confirmed that the COX2 S565 acetylation detected by the prepared monoclonal antibody 44C7C8 in the blood cells of the Alzheimer's patient was reduced compared to a control (FIG. 6A).

Figure 6B:
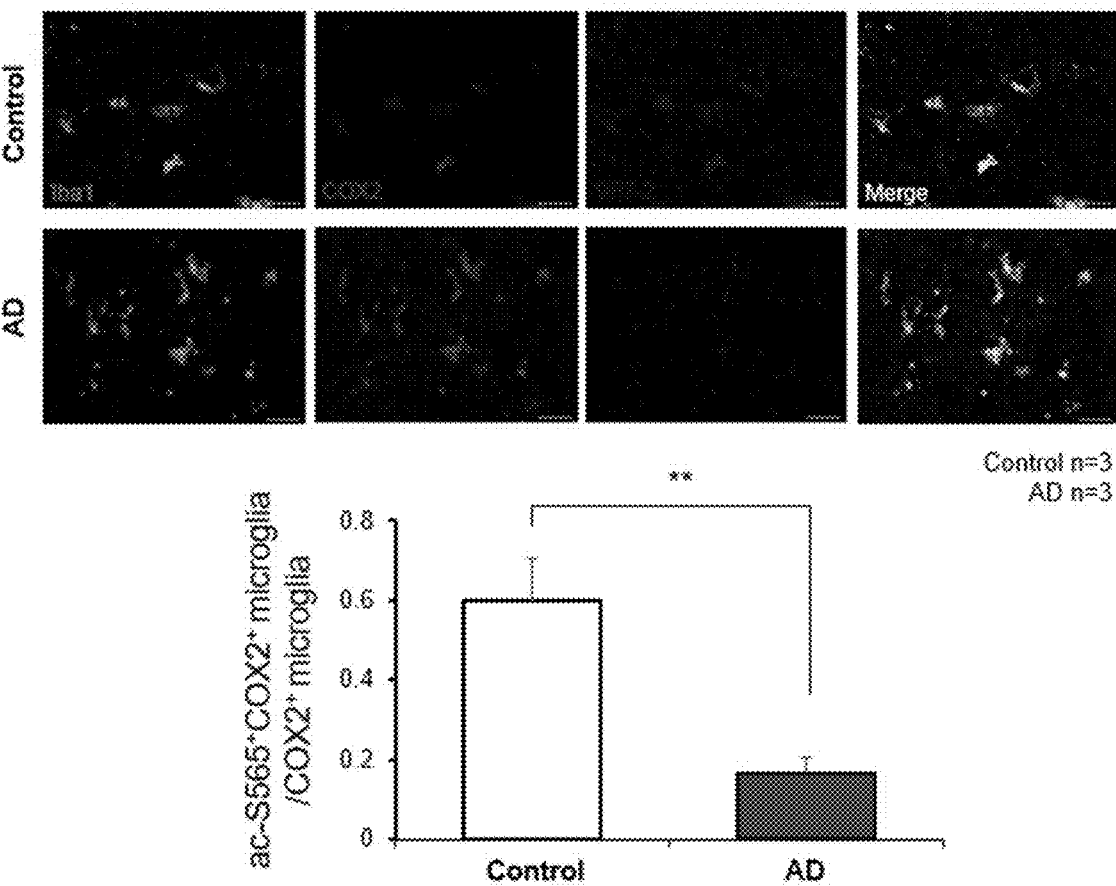

In addition, the present inventors reconfirmed the degree of COX2 S565 acetylation in microglia of the brain tissue of the Alzheimer's patient using the prepared monoclonal antibody 44C7C8. As a result, it was confirmed that the COX2 S565 acetylation detected by the prepared monoclo-nal antibody 44C7C8 was reduced in the microglia of the Alzheimer's patient compared to the control, like the blood cell results of FIG. 6A (FIG. 6B).

Therefore, these results confirmed that S565 acetylation was reduced in a region of GCPFTSacFSVPD (SEQ ID NO: 4) of COX2, which was detected by the prepared monoclo-nal antibody 44C7C8 in blood cells and microglia of the Alzheimer's patient.

Through the results, it was confirmed that the degree of S565 acetylation of COX2 protein detected by the mono-clonal antibody 44C7F5 in blood cells and microglia of the Alzheimer's patient was significantly reduced, and it was confirmed that the ratio of the S565 acetylated COX2 protein to the total COX2 protein in the microglia of the brain tissue of the Alzheimer's patient was significantly low as compared with the control. The result coincided with the Alzheimer's animal result of FIG. 5 and suggested the applicability of the ratio of the S565 acetylated COX2 protein to the total COX2 protein as a diagnostic marker for neurodegenerative diseases.

INDUSTRIAL APPLICABILITY

According to the present invention, an antibody or a functional fragment thereof specifically binds to an acety-lated residue of COX2 protein and thus can be very effec-tively used for diagnosing neurodegenerative diseases, inflammatory diseases, and the like in which the degree of acetylation of S565 residue of the COX2 protein is reduced.

What is claimed is:

1. An antibody or a functional fragment thereof that specifically recognizes the acetylation of cyclooxygenase 2 (COX2) protein;

wherein the antibody or the functional fragment thereof is an antibody or a functional fragment thereof comprising an antibody light chain variable region (VL) having a complementarity determining region (CDR) L1 including an amino acid sequence having SEQ ID NO: 5, a complementarity determining region (CDR) L2 including an amino acid sequence having SEQ ID NO: 6, and a complementarity determining region (CDR) L3 including an amino acid sequence having SEQ ID NO: 7 and an antibody heavy chain variable region (VH) having a complementarity determining region (CDR) H1 including an amino acid sequence having SEQ ID NO: 8, a complementarity determining region (CDR) H2 including an amino acid sequence having SEQ ID NO: 9, and a complementarity determining region (CDR) H3 including an amino acid sequence having SEQ ID NO: 10; or an antibody or a functional fragment thereof comprising an antibody light chain variable region (VL) having a complementarity determining region (CDR) L1 including an amino acid sequence having SEQ ID NO: 21, a complementarity determining region (CDR) L2 including an amino acid sequence having SEQ ID NO: 22, and a complementarity determining region (CDR) L3 including an amino acid sequence having SEQ ID NO: 23 and an antibody heavy chain variable region (VH) having a complementarity determining region (CDR) H1 including an amino acid sequence having SEQ ID NO: 24, a complementarity determining region (CDR) H2 including an amino acid sequence having SEQ ID NO: 25, and a complementarity determining region (CDR) H3 including an amino acid sequence having SEQ ID NO: 26; or wherein the antibody or the functional fragment thereof is an antibody or a functional fragment thereof comprising a light chain variable region (VL) including an amino acid sequence having SEQ ID NO: 11 and a heavy chain variable region (VH) including an amino acid sequence having SEQ ID NO: 12; or an antibody or a functional fragment thereof comprising a light chain variable region (VL) including an amino acid sequence having SEQ ID NO: 27 and a heavy chain variable region (VH) including an amino acid sequence having SEQ ID NO: 28.

2. The antibody or the functional fragment thereof of claim 1, wherein the acetylation is acetylation in S565 residue of cyclooxygenase 2 (COX2) protein defined by SEQ ID NO: 1.

3. The antibody or the functional fragment thereof of claim 1, wherein the epitope of the antibody is a peptide including an amino acid sequence represented by SEQ ID NO: 2 and consisting of 9 to 50 amino acids.

4. The antibody or the functional fragment thereof of claim 1, wherein the epitope of the antibody is a peptide consisting of an amino acid sequence represented by SEQ ID NO: 3 or SEQ ID NO: 4.

5. The antibody or the functional fragment thereof of claim 1, wherein the antibody is selected from the group consisting of IgG, IgA, IgM, IgE and IgD.

6. The antibody or the functional fragment thereof of claim 1, wherein the functional fragment of the antibody is selected from the group consisting of a diabody, Fab, Fab', F(ab)2, F(ab')2, Fv and scFv.

7. A polynucleotide encoding the antibody or the functional fragment thereof of claim 1.

8. A vector comprising the polynucleotide of claim 7.

9. A host cell transformed with the vector of claim 8.

10. A method for preparing an antibody or a functional fragment thereof that specifically recognizes acetylation of cyclooxygenase 2 (COX2) protein, comprising steps of producing a polypeptide including light chain and heavy chain variable regions by culturing the cell of claim 9 under a condition in which the polynucleotide is expressed, and recovering the polypeptide from the cell or a culture medium culturing the cell.

11. A composition for diagnosing neurodegenerative diseases comprising the antibody or the functional fragment thereof of claim 1.

12. The composition of claim 11, wherein the neurodegenerative diseases are one or more selected from the group consisting of Alzheimer's disease, Parkinson's disease, progressive supranuclear palsy, multiple system atrophy, olivine-pony-cerebellar atrophy (OPCA), Shay-Drager syndrome, striatal-nigular degeneration, Huntington's disease, amyotrophic lateral sclerosis (ALS), essential tremor, cortical-basal nucleus degeneration, diffuse Lewy body disease, Parkinson's-ALS-dementia complex, Nieman-Pick's disease, Pick's disease, cerebral ischemia and cerebral infarction.

13. A kit for diagnosing neurodegenerative diseases comprising the antibody or the functional fragment thereof of claim 1.

14. A composition for diagnosing inflammatory diseases comprising the antibody or the functional fragment thereof of claim 1.

15. The composition of claim 14, wherein the inflammatory diseases are one or more selected from the group consisting of dermatitis, allergy, atopic dermatitis, asthma, conjunctivitis, rhinitis, otitis media, sore throat, tonsillitis, pneumonia, gastric ulcer, gastritis, Crohn's disease, inflammatory bowel disease, lupus, hepatitis, cystitis, nephritis, sjogren's syndrome, uveitis, ankylosing spondylitis, endometritis, multiple sclerosis, sepsis, septic shock, chronic obstructive pulmonary disease and arthritis.

16. A method for diagnosing neurodegenerative diseases comprising steps of:
   a) obtaining a sample from a subject;
   b) measuring an acetylation level of COX2 protein by adding the antibody or the functional fragment thereof of claim 1 to the sample; and
   c) comparing the acetylation level of the COX2 protein with that of a normal subject, and determining that a subject having a reduced acetylation level of the COX2 protein compared to the normal subject suffers from neurodegenerative diseases.

17. A method for diagnosing inflammatory diseases comprising steps of:
   a) obtaining a sample from a subject;
   b) measuring an acetylation level of COX2 protein by adding the antibody or the functional fragment thereof of claim 1 to the sample; and
   c) comparing the acetylation level of the COX2 protein with that of a normal subject, and determining that a subject having a reduced acetylation level of the COX2 protein compared to the normal subject suffers from inflammatory diseases.

* * * * *